United States Patent
Eriksson et al.

(10) Patent No.: US 9,939,418 B2
(45) Date of Patent: Apr. 10, 2018

(54) SYSTEM AND METHOD FOR MULTIPHASE FLOW MEASUREMENTS

(71) Applicant: FMC Kongsberg Subsea AS, Kongsberg (NO)

(72) Inventors: Anders Eriksson, Göteborg (SE); Larisa Beilina, Mölndal (SE)

(73) Assignee: FMC Kongsberg Subsea AS, Kongsberg (NO)

( * ) Notice: Subject to any disclaimer, the term of this patent is extended or adjusted under 35 U.S.C. 154(b) by 71 days.

(21) Appl. No.: 15/118,833

(22) PCT Filed: Feb. 12, 2015

(86) PCT No.: PCT/EP2015/053002
§ 371 (c)(1),
(2) Date: Aug. 12, 2016

(87) PCT Pub. No.: WO2015/121365
PCT Pub. Date: Aug. 20, 2015

(65) Prior Publication Data
US 2017/0052167 A1 Feb. 23, 2017

(30) Foreign Application Priority Data

Feb. 14, 2014 (NO) .................................. 20140185

(51) Int. Cl.
*G01N 33/28* (2006.01)
*G01F 1/66* (2006.01)
(Continued)

(52) U.S. Cl.
CPC ........... *G01N 33/2823* (2013.01); *G01F 1/56* (2013.01); *G01F 1/66* (2013.01); *G01F 1/74* (2013.01); *G01N 22/00* (2013.01); *G01N 27/02* (2013.01)

(58) Field of Classification Search
CPC .... G01N 33/2823; G01N 22/00; G01N 27/02; G01F 1/56; G01F 1/66; G01F 1/74
See application file for complete search history.

(56) References Cited

U.S. PATENT DOCUMENTS 3,213,439 A 10/1965 Atkinson
6,831,470 B2 * 12/2004 Xie ..................... G01N 33/2823
324/637
(Continued)

FOREIGN PATENT DOCUMENTS

DE 195 00 559 A1 7/1996
WO WO 93/00591 A1 1/1993
(Continued)

OTHER PUBLICATIONS

L.F. Chen, C.K. Ong, C.P. Neo, V.V. Varadan and V.K. Varadan, *Microwave Electronics: Measurement and Materials Characterization* (2004 John Wiley & Sons, Ltd.).

*Primary Examiner* — Hezron E Williams
*Assistant Examiner* — David Z Huang

(57) ABSTRACT

A system, method and hydrocarbon processing facility for determining at least one parameter of a multiphase fluid (1) comprising hydrocarbons flowing in a conduit (2) of a hydrocarbon processing facility, which system comprises: said conduit; at least one coaxial measurement probe (3), which comprises at least one probe conductor, a probe shield (7) arranged outside of the at least one probe conductor, which at least one measurement probe is mounted to the conduit for measuring signals indicative of at least one physical property of the fluid- and comprises a first, open-ended terminal (8) where the at least one probe conductor and the probe shield are exposed to the flowing fluid when the system is in operation; and a signal processor (4) for interpreting the signals to determine the at least one parameter. The at least one measurement probe comprises a second (Continued)

terminal (9), and the system comprises a signal line (10) for conveying the signals from the at least one measurement probe to the signal processor, which signal line is connected to the at least one measurement probe at a predetermined position (P) in between the first terminal and the second terminal.

18 Claims, 17 Drawing Sheets

(51) Int. Cl.
  *G01F 1/74* (2006.01)
  *G01N 22/00* (2006.01)
  *G01F 1/56* (2006.01)
  *G01N 27/02* (2006.01)

(56) References Cited

U.S. PATENT DOCUMENTS

| | | |
|---|---|---|
| 2009/0000393 A1 | 1/2009 | Nyfors et al. |
| 2009/0204346 A1 | 8/2009 | Xie |
| 2017/0052048 A1* | 2/2017 | Eriksson .................. G01F 1/66 |

FOREIGN PATENT DOCUMENTS

| | | |
|---|---|---|
| WO | WO 2007/129208 A2 | 11/2007 |
| WO | WO 2007/129897 A1 | 11/2007 |

* cited by examiner

| Salinity | Low pole amplitude @~80MHz($Z_c=0$) | High pole amplitude @~260MHz($Z_c=0$) |
|---|---|---|
| 0.1% salinity | 0.5276 | 0.6231 |
| 0.01% salinity | 0.8794 (0.3518 change) | 0.8572 (0.2341 change) |
| 0.001% salinity | 0.9239 (0.0445 change) | 0.8844 (0.0272 change) |
| Salinity | Low pole amplitude @~80MHz($Z_c=1$) | High pole amplitude @~260MHz($Z_c=1$) |
| 0.1% salinity | 0.06086 | 0.1415 |
| 0.01% salinity | 0.2159 (0.1550 change) | 0.2504 (0.1089 change) |
| 0.001% salinity | 0.234 (0.0181 change) | 0.2624 (0.0120 change) |

Fig. 17

| Salinity | Pole amplitude @~185MHz($Z_c=0$) |
|---|---|
| 6% salinity | 0.3792 |
| 7% salinity | 0.3244 |
| 8% salinity | 0.2752 |
| Salinity | Pole amplitude @~185MHz($Z_c=1$) |
| 6% salinity | 0.4295 |
| 7% salinity | 0.3833 |
| 8% salinity | 0.3425 |

Fig. 22

SYSTEM AND METHOD FOR MULTIPHASE FLOW MEASUREMENTS

FIELD OF THE INVENTION

The present invention relates to a system and a method for determining at least one parameter of a multiphase fluid, i.e. a multi-component mixture of at least one gas and at least one liquid, comprising hydrocarbons flowing in a conduit of a hydrocarbon processing facility.

In particular, the invention relates to a system comprising:
said conduit;
at least one measurement probe, which comprises:
at least one probe conductor,
a probe shield arranged outside of the at least one probe conductor, which at least one measurement probe is mounted to the conduit for measuring signals indicative of at least one physical property of the fluid and comprises a first, open-ended terminal where the probe conductor and the probe shield are exposed to the flowing fluid when the system is in operation; and
a signal processor for interpreting the signals to determine the at least one parameter.

The invention also relates to a hydrocarbon processing facility comprising such a system.

BACKGROUND

WO 2007/129897 discloses an apparatus for determining the flow rates and fractions of a fluid comprising a multiphase fluid in a pipe. The apparatus comprises a coaxial conductor with an inner conductor, screen and dielectric insulator mounted open ended flush with the pipe wall (cf. FIG. 13). By transmitting a signal on the coaxial conductor and analysing the reflected signal on the coaxial line due to the impedance difference between the coaxial cable and the pipe containing the multiphase fluid, the fractions of the multiphase mixture can be determined. This device is particularly suited for performing dielectric measurement of liquid films along the pipe wall at wet gas flow conditions.

WO 2007/129208 A2 discloses a microwave resonator exhibiting an impedance having a value which depends on a product to be examined by the resonator.

U.S. Pat. No. 3,213,439 A discloses a level indicating device comprising an outer cylindrical conductor 37, an inner conductor 38 and plastic or other insulating material 43 sealing the space between the conductors 37 and 38.

DE 19500559 A1 discloses a resonator comprising an outer conductor 1 and an inner conductor 2 which, at a first end of the resonator, are connected to coaxial plates of a stray field condenser 3, which plates are separated by a gap allowing a stray field to extend outside of the resonator.

US 2009/0204346 A1 discloses a system for measuring properties of a multiphase mixture flowing in a pipe. The system comprises open-ended coaxial probes which are flush mounted at the pipe wall.

WO 93/00591 A1 discloses an apparatus for measuring the complex permittivity and conductivity of a dielectric material. The apparatus comprises a structure which can be made to resonate at a radio or microwave frequency when in contact with or adjacent the dielectric material.

A problem with prior art systems and methods of the above-discussed type, however, is that they require extensive calibration.

One object of the present invention is to alleviate this problem and provide a system and a method which facilitate calibration.

Another problem with prior art systems is that they are susceptible to temperature and erosion induced measurement errors. Therefore, another object of the present invention is to provide a system and a method which can compensate for such errors.

Yet a further object of the invention is to provide a system comprising a robust and reliable measurement probe.

SUMMARY OF THE INVENTION

The system according to the invention is characterised in that the at least one measurement probe comprises a second terminal, and in that the system comprises a signal line for conveying the signals from the at least one measurement probe to the signal processor, which signal line is connected to the at least one measurement probe at a predetermined position in between the first terminal and the second terminal.

Consequently, the predetermined position is located at a first predetermined distance from the first terminal and a second predetermined distance from the second terminal.

It may be advantageous to locate said predetermined position within a distance from the middle of the at least one measurement probe which is within 10-20% of the length of the probe. It may be particularly advantageous to arrange the predetermined position half-way between the first terminal and the second terminal, i.e. such that said first predetermined distance is equal to said second predetermined distance.

The method according to the invention comprises the steps of:
mounting the at least one measurement probe at the conduit (2) such that the probe conductor and the probe shield, at the first terminal, are exposed to the flowing fluid,
using the at least one measurement probe, measuring signals indicative of at least one physical property of the fluid,
using a signal line connected to the at least one probe at a predetermined position in between the first terminal and the second terminal, conveying the signals from the at least one measurement probe to a signal processor, and
using the signal processor, processing the signals to determine the at least one parameter.

The at least one parameter may comprise any one of a flow rate of the fluid, a volume fraction of the fluid, a thickness of a liquid layer or film covering an inside wall of the conduit, and a composition of the liquid layer and/or film.

The measurement probe effectively acts as a resonator which is probed by the signal line at a position in between the first and second terminals. Whereas the first terminal is open-ended such that the measurement probe, at this first terminal, is subjected to an impedance or load which is determined by the physical properties of the fluid in the conduit, the second terminal may be subjected to any pre-determined load or impedance which gives a suitable resonance in the measurement probe. Preferably, the probe conductor and the probe shield are short-circuited at the second terminal such that the measurement probe would act as a quarter-wave resonator. However, the probe conductor and the probe shield may alternatively be electrically isolated from each other at the second terminal, in which case the measurement probe will act as a half-wave probe.

Consequently, the system according to the invention can be used to measure any physical property of the fluid which influences the impedance of the first terminal of the probe.

In evaluating the signal of the probe, a suitable model for the fluid is advantageously used, e.g. as disclosed in *Effect of salinity on the dielectric properties of water*, D H Gadani et al., Indian Journal of Pure & Applied Physics, Vol. 50, June 2012, pp. 405-410, and *Static Analysis of an Open Ended Coaxial Line Terminated by Layered Media*, SIQI FAN et al., IEEE Transactions on instrumentation and measurement. VOL. 39, No. 2, April 1990, pp. 435-437, whereby the adaptation of the model to the measured signal will yield information on the physical parameters of the fluid.

If the probe conductor and the probe shield are short-circuited at the second terminal, the signal line should preferably be connected to the measurement probe at a position which is approximately at the middle of the measurement probe. At this position, the resonance signal will display a maximum, which allows for measuring very small changes of the fluid property, e.g. small changes of the water content in the fluid.

Preferably, the measurement probe operates within a frequency interval of approximately 100 MHz-600 MHz.

As compared to prior art systems, which measure phase and magnitude response directly, the measurement probe according to the invention is robust and rigid which makes it easy to calibrate. Advantageously, a temperature reference or calibration probe based on the same principle as the measurement probe is included in the system.

A typical use of the system and method according to the invention is in a wet gas sensor application, where the open-ended terminal of the measurement probe is exposed to a liquid film layer backed by underlying wet gas. The system may also be used in a full multiphase meter application.

It may be advantageous to include a plurality of measurement probes displaying different coaxial radii into the system such that different penetration depths into the fluid are obtained. This will allow each measurement probe to measure unique data such that unknown physical fluid parameters can be extracted, e.g. using a regularization method or an inverse algorithm method that solves out desired unknowns.

It may be advantageous to include into the system a first measurement probe in which the probe conductor, at the second terminal, is galvanically coupled to the probe shield, and a second measurement probe comprising, at the second terminal, a resistive element providing a pre-determined impedance between the probe conductor and the probe shield.

DESCRIPTION OF THE DRAWINGS

In the following, specific embodiments of the present invention will be described in more detail with reference to the attached drawings.

FIGS. 13-35 disclose simulated reflection signals of the measurement probes according to FIGS. 1 and 12.

DETAILED DESCRIPTION OF THE INVENTION

Figure 1:
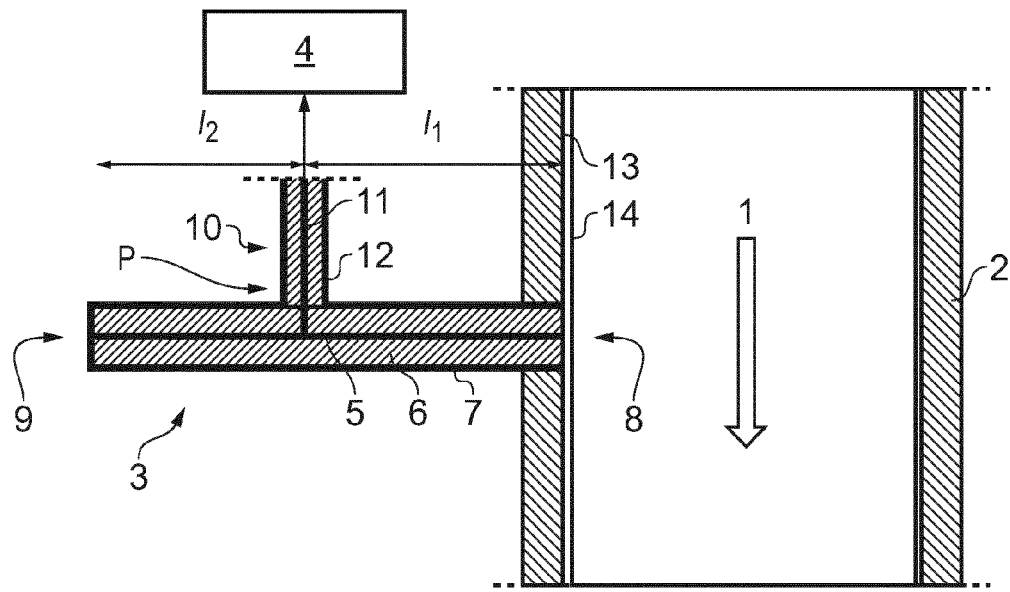
FIG. 1 is a schematic illustration of a measurement probe according to one embodiment of the invention.

FIG. 1 schematically illustrates a system for determining at least one parameter of a multiphase fluid 1 comprising hydrocarbons flowing in a conduit 2 of a hydrocarbon processing facility. The hydrocarbon processing facility may be a hydrocarbon production facility, such as an offshore or an on-shore hydrocarbon well complex, a hydrocarbon transport facility, or any other type of facility where hydrocarbons are handled.

The system comprises said conduit 2 and a coaxial measurement probe 3, which is mounted to the conduit 2 for measuring signals indicative of at least one physical property of the fluid 1.

The system also comprises a sensor or signal processor 4 for interpreting the signals to determine the at least one parameter, and a signal line 10 for conveying the signals from the measurement probe 3 to the signal processor 4. Such signal processors 4 are known as such and will not be disclosed in any detail here. However, as is known in the art, it may be advantageous to provide the signal processor 4 with a processing unit, e.g. a central processing unit (CPU), to implement the interpretation of the signals. Furthermore, or alternatively, it may be advantageous to provide the signal processor 4 with a storage unit, such as a non-volatile memory, and/or a display unit, such as a screen, to store and present the signals, respectively. Also, it may be advantageous to provide the signal processor 4 with input and output means to enable communication between the signal processor 4 and other equipment, e.g. further signal processing means.

Said at least one parameter may comprise any one of: the volume fraction of the fluid 1, and the thickness and the composition of a liquid layer or film 14 of the fluid 1 covering an inside wall 13 of the conduit 2.

The measurement probe 3 comprises an inner, axial probe conductor 5, a dielectric insulator 6, which is arranged outside of the probe conductor 5, and an outer probe shield 7, which is arranged outside of the dielectric insulator 6. Consequently, the probe conductor 5, the insulator 6 and the probe shield 7 have a coaxial relationship. The probe shield 7 is preferably grounded. Also, it may be advantageous to galvanically connect the probe shield 7 to the conduit.

The probe 3 extends through the conduit 2 and comprises a first, open-ended terminal 8 where the probe conductor 5 and the probe shield 7 are exposed to the flowing fluid 1 when the system is in operation. At the first terminal 8, the probe conductor 5, the probe shield 7 and the insulator 6 may advantageously be arranged coplanar with the inside wall 13 of the conduit 2 such that the probe 3 does not disturb the fluid 1, e.g. the liquid layer 14, and, in addition, is not easily eroded by the fluid 1. If the conduit 2 is a small diameter pipe, the exposed surface of the first terminal 8 may be given a concave shape such that the exposed surface can be arranged flush with the inside wall 13 of the conduit 2.

Alternatively, the probe 3 may extend beyond the inside wall 13 such that the first terminal 8 extends a predetermined distance from the wall 13.

The probe 3 also comprises a second, short-circuited terminal 9, where the probe conductor 5 and the probe shield 7 are electrically connected to each other. Consequently, due to the open-ended first terminal 8 and the short-circuited second terminal 9, the probe 3 will act as an open-ended quarter-wave resonator.

The signal line 10 comprises a signal line conductor 11, which is connected to the probe conductor 5, and a signal line shield 12 which is connected to the probe shield 7. The signal line 10 is connected to the probe 3 at a predetermined position P in between the first terminal 8 and the second terminal 9, which position defines a measurement reference plane. In other words, the signal line 10 is positioned at a pre-determined, first distance $l_1$ from the first terminal 8, and at a predetermined, second distance $l_2$ from the second terminal 9.

Figure 2:
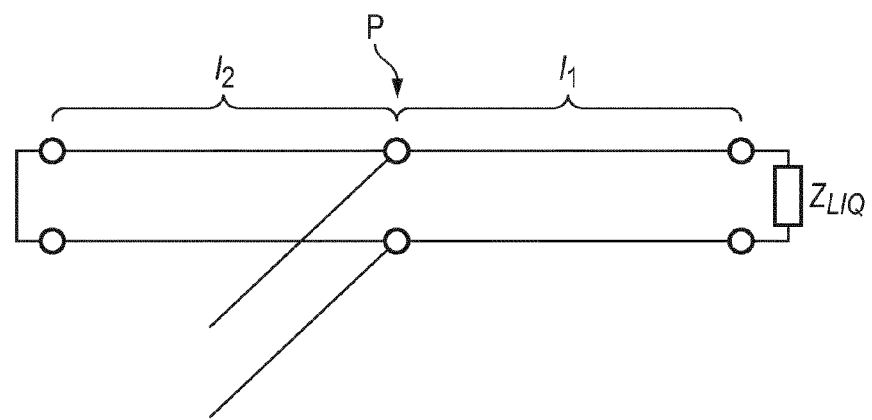
FIG. 2 is a schematic illustration of an equivalent circuit for the measurement probe according to FIG. 1.

FIG. 2 discloses an equivalent circuit for the reflection topology of the probe 3 when measuring at least one physical property of the liquid layer 14.

In FIGS. 1 and 2 the signal line conductor 11 is disclosed to form a galvanic connection to the probe conductor 5. However, the signal line conductor 11 may alternatively form a capacitive or an inductive connection to the probe conductor 5. Similarly, the signal line shield 12 may form a galvanic, a capacitive or an inductive connection with the probe shield 7.

The analytical tools for describing the measured reflection coefficient S11 of the measurement probe 3 is given by the general impedance transformation formula:

$$Z_{in} = Z_0 \frac{Z_L + Z_0 \tanh(\gamma l)}{Z_0 + Z_L \tanh(\gamma l)} \quad \text{[Equation 1]}$$

where $Z_0$ is the characteristic impedance of the probe 3, $Z_L$ is the load impedance of the open-ended terminal 8, $\gamma$ is the wavenumber of the probe 3, and l is the physical length of the probe 3 from the reflection position to the measurement reference plane.

In the present case, the impedance looking from the position P towards the second terminal 9 of the measurement probe 3 can be expressed as:

$$Z_{in}^{left} = Z_0 \tan h(\gamma l_{left}) \quad \text{[Equation 2]}$$

where $l_{left}$ is the distance from the position P to the second terminal 9.

The impedance looking from the position P towards the first terminal 8 can be expressed as:

$$Z_{in}^{right} = Z_0 \frac{Z_{LIQ} + Z_0 \tanh(\gamma l_{right})}{Z_0 + Z_{LIQ} \tanh(\gamma l_{right})} \quad \text{[Equation 3]}$$

where $l_{right}$ is the distance from the position P to the first terminal 8, and $Z_{LiQ}$ is the impedance at the open-ended first terminal 8, i.e. the impedance of the liquid layer 14 in the present case. In modelling the measurement system, any accurate model of fluid at the first terminal 8 can be used to model $Z_{LIQ}$.

For reflection measurements, it may be advantageous to set $l_{left} = l_{right}$ i.e. to set the reference plane at the middle of the measurement probe 3. However, the measurement plane P can, in principle, be chosen to be at any suitable position in between the terminals 8 and 9. However, preferably the measurement plane P is positioned within a distance of 10-20% from the middle of the probe 3.

FIG. 2 schematically illustrates an equivalent circuit for the measurement probe 3 where the reference plane, defined by the position P, is chosen to be in the middle of the probe.

In order to calibrate the measurement probe according to the invention, the open-ended terminal 8 is exposed to one or, preferably, a plurality of known environments and the reflection signal for these calibration cases are measured. For example, the open-ended terminal 8 may be exposed to air and the reflection signal thus monitored may be associated with a first calibration standard. In addition, or alternatively, the open-ended terminal 8 may be exposed to distilled water, or to any other liquid having a dielectric constant displaying a large real part component and a small imaginary part component, and the reflection signal thus monitored may be associated with a second calibration standard. In addition, or alternatively, the open-ended terminal 8 may be exposed to saline water having a known salinity (preferably a salinity of >5%), and the reflection signal thus monitored may be associated with a third calibration standard.

During this calibration procedure, temperature must be well controlled, since electrical parameters of liquids may be sensitive to temperature.

Figure 3:
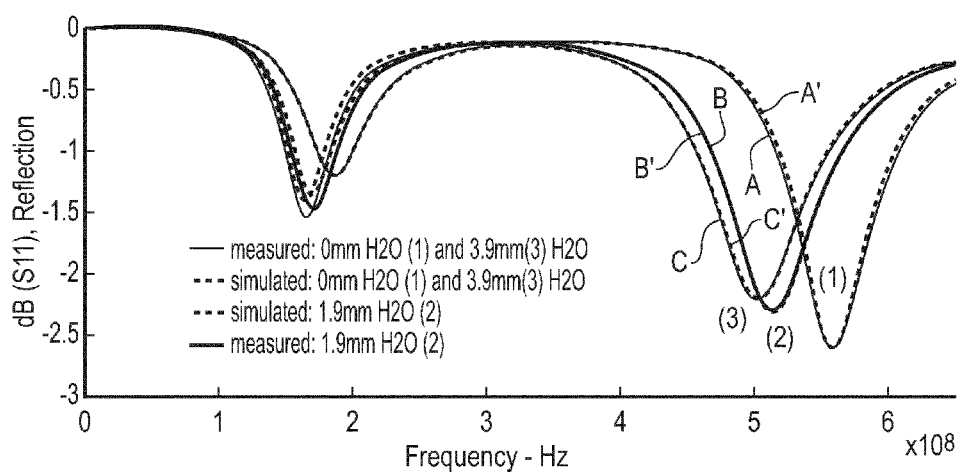
FIG. 3 illustrates measured and simulated reflection signals of a measurement probe according to the invention.

FIG. 3 illustrates measured reflection signals A, B, C for three different operation conditions, or calibration standards or cases, using a measurement probe 3 according to FIG. 1. In this particular case, the probe was 24 cm long, the probe conductor 5 had a diameter of 5 mm, the probe shield 7 a diameter of 10 mm, and the dielectric layer 6 was made of araldite epoxy. The measurement plane P was positioned in the middle of the probe 3.

During the first calibration case, which resulted in the reflection signal A, the first terminal 8 of the measurement probe 3 was exposed to air. During the second calibration case, which resulted in the reflection signal B, the first terminal 8 was exposed to a 1.9 mm thick layer of freshwater. During the third calibration case, which resulted in the reflection signal C, the first terminal 8 was exposed to a 3.9 mm thick layer of freshwater. During all calibration cases, the temperature was 25 degrees centigrade. The freshwater used for the second and third calibration cases had a salinity of 0.0001%.

Figure 4:
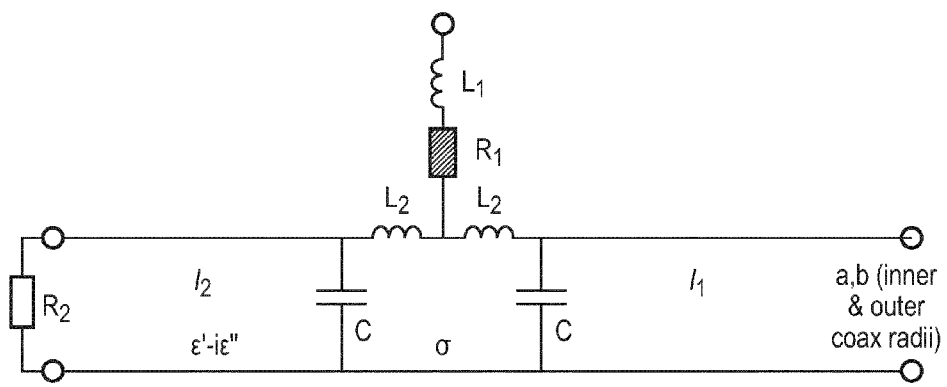
FIG. 4 is an illustration of an equivalent circuit of a resonator model used for calibration of a measurement probe according to the invention.

When calibrating the probe 3, a resonator model according to the equivalent circuit of FIG. 4 was used and the parameters $L_1$ and $L_2$ were fine tuned to get a good fit between simulated and measured reflection signals. Curve A' is the simulated reflection signal corresponding to the first calibration case, curve B' is the simulated reflection signal corresponding to the second calibration case, and curve C' is the simulated reflection signal corresponding to the third calibration case. As is evident from FIG. 3, a very good fit between the measured reflection signals and the simulated reflection signals is achieved, thus providing a simple and accurate calibration of the probe 3.

According to an alternative embodiment of the measurement probe 3, the first and second terminals are both open-ended, in which case the probe will act as a half-wave resonator rather than a quarter-wave resonator. In such an embodiment, the signal line 10 should not be connected to the probe conductor and the probe shield in the middle of the probe, since the reflection signal will have a reflection minima at that position. Preferably, for a measurement probe in which the first and second terminals are both open-ended, the signal line 10 should preferably be connected to the measurement probe at a position in between the middle of the probe and the second terminal. The half-wave probe is calibrated in the same way as the quarter-wave probe with the exception that a half-wave model rather than a quarter-wave model is used to model the reflection signal.

Figure 5:
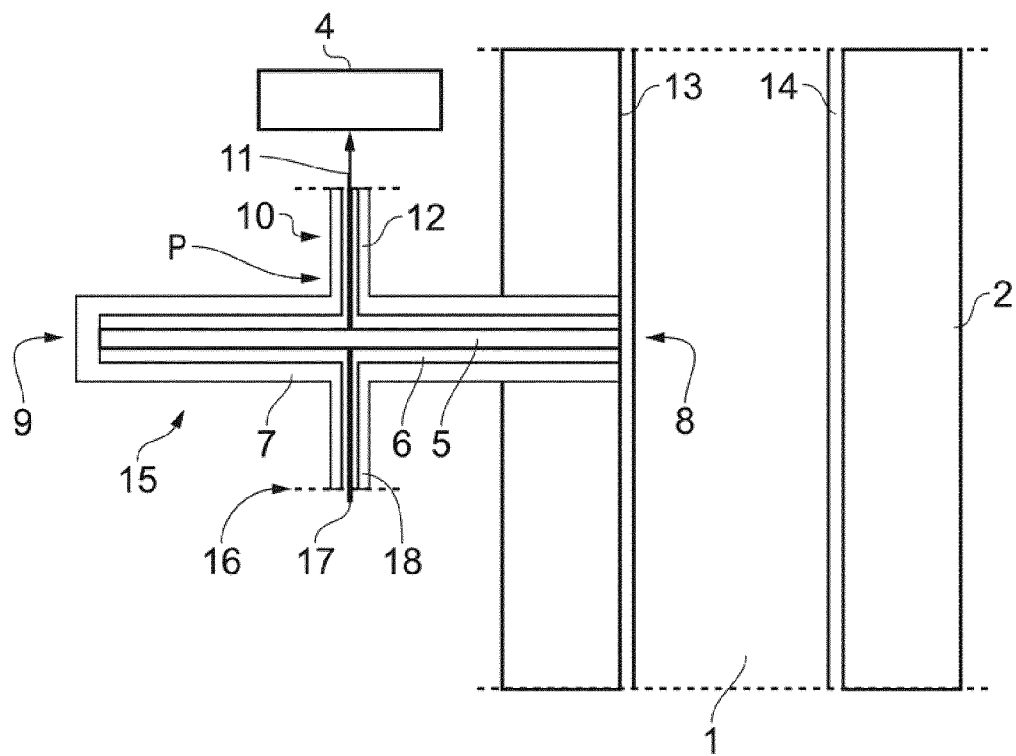
FIG. 5 is a schematic illustration of a measurement probe according to a second embodiment of the invention.

FIG. 5 schematically illustrates a measurement probe 15 according to a second embodiment of the invention in which a second signal line 16 is connected to the probe 15 at the predetermined position P, thus enabling an open-ended quarter-wave measurement resonator having a transmission topology. In analogy with the first signal line 10, the second signal line 16 comprises a signal line conductor 17 which is connected to the probe conductor 5 and a signal line shield 18 which is connected to the probe shield 7.

Figure 6:
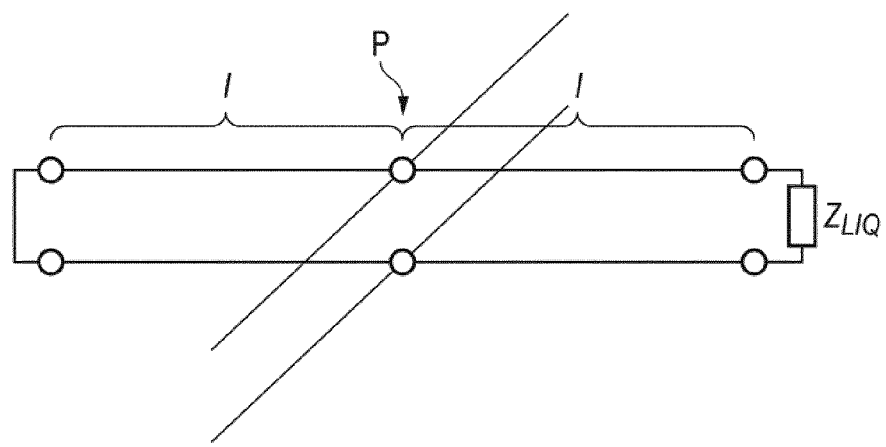
FIG. 6 is a schematic illustration of an equivalent circuit for the measurement probe according to FIG. 5.

FIG. 6 schematically illustrates an equivalent circuit of the probe 15 where the reference plane, defined by the position P, is chosen to be in the middle of the probe.

According to an alternative embodiment of the system, at least two open-ended measurement probes having different inner and outer coaxial diameters are employed. The different inner and outer coaxial diameters will result in different penetration depths of the electromagnetic field emerging from the probes. This will allow each measurement probe to measure unique data such that unknown physical fluid parameters can be extracted, e.g. using a regularization method or an inverse algorithm method that solves out desired unknowns. The number of measurement probes used in the system is preferably adapted to the number of fluid parameters the system is employed to measure such that the values for all unknown parameters can be solved simultaneously.

Small changes in the physical length of the probe conductor 5 and the probe shield 7 influence the resonance frequency of the measurement probe 3. Such changes in physical length may, for example, be caused by thermal expansion. Therefore, it may be advantageous to compensate for this temperature influence by incorporating a temperature reference probe 19 into the system.

Figure 7:
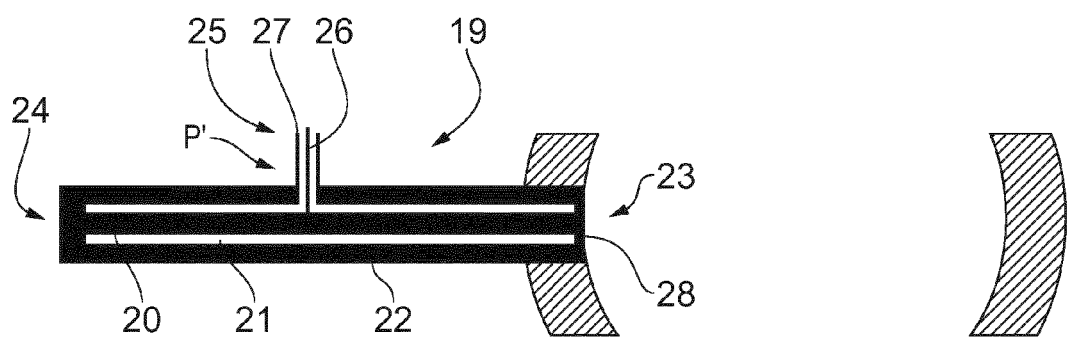
FIG. 7 is a schematic illustration of a reference probe according to a one embodiment of the invention.

FIG. 7 discloses an embodiment of such a temperature reference probe 19. The reference probe 19 and its arrangement are similar to that of the above-described measurement probe 3. In particular, the reference probe 19 comprises an inner, axial probe conductor 20, a dielectric insulator 21, which is arranged outside of the probe conductor 20, and a second, cylindrical probe shield 22, which is arranged outside of the dielectric insulator 21. The probe 19 extends through the conduit 2 and comprises a first terminal 23 where the probe conductor 20 and the probe shield 22 are exposed to the flowing fluid 1 when the system is in operation. The probe 19 also comprises a second, short-circuited terminal 24, where the probe conductor 20 and the probe shield 22 are electrically connected to each other. A signal line 25 is connected to the probe 19 at a predetermined position P' in between the first terminal 23 and the second terminal 24, which position defines a measurement reference plane. The signal line 25 comprises a signal line conductor 26, which is connected to the probe conductor 20, and a signal line shield 27 which is connected to the probe shield 22.

The reference probe 19 has he same physical dimensions, including the same length, as the above-discussed measurement probe 3. Also, in the disclosed embodiment, the position P' of the signal line 25 is the same as the position P of the signal line 10 of the probe 3. Consequently, the reference probe 19 displays the same dimensions and signal line 25 placement P' as the measurement probe 3. Alternatively, the placement P' of the signal line 25 may be different as compared to the placement P.

However, at the first terminal 23 the probe conductor 20 and the probe shield 22 are short-circuited by means of a thin short-circuit buffer 28. Consequently, the reference probe 19 is, electrically, a half-wave resonator, and the resonance frequency of the reference probe 19 is only a function of the temperature. By positioning the reference probe 19 such that it is exposed to the same temperature as the measurement probe 3, the contribution of the temperature to the measured signal can be deduced by comparing the signals from the measurement probe 3 and the temperature reference probe 19. Consequently, the first reference probe 19 is exposed to the same temperature environment as the measurement probe 3, thus enabling said signals to be compensated for temperature induced length variations of the measurement probe 3.

Figure 8:
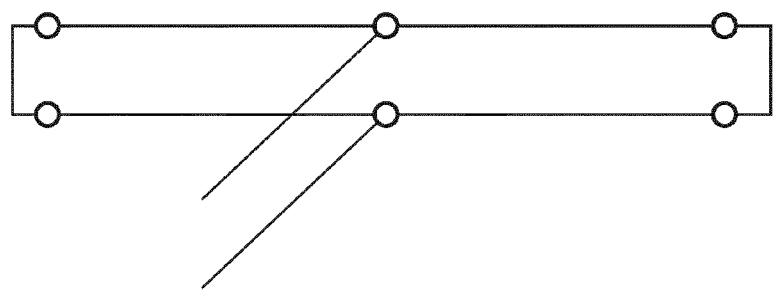
FIG. 8 is a schematic illustration of an equivalent circuit for the reference probe according to FIG. 7.

FIG. 8 schematically illustrates an equivalent circuit for the temperature reference probe 19.

The physical length of the probe conductor 5 and the probe shield 7 may also decrease due to erosion caused by the flowing fluid. According to one embodiment of the invention, this is compensated for by using two measurement probes displaying different lengths as is disclosed in FIG. 9.

Figure 9:
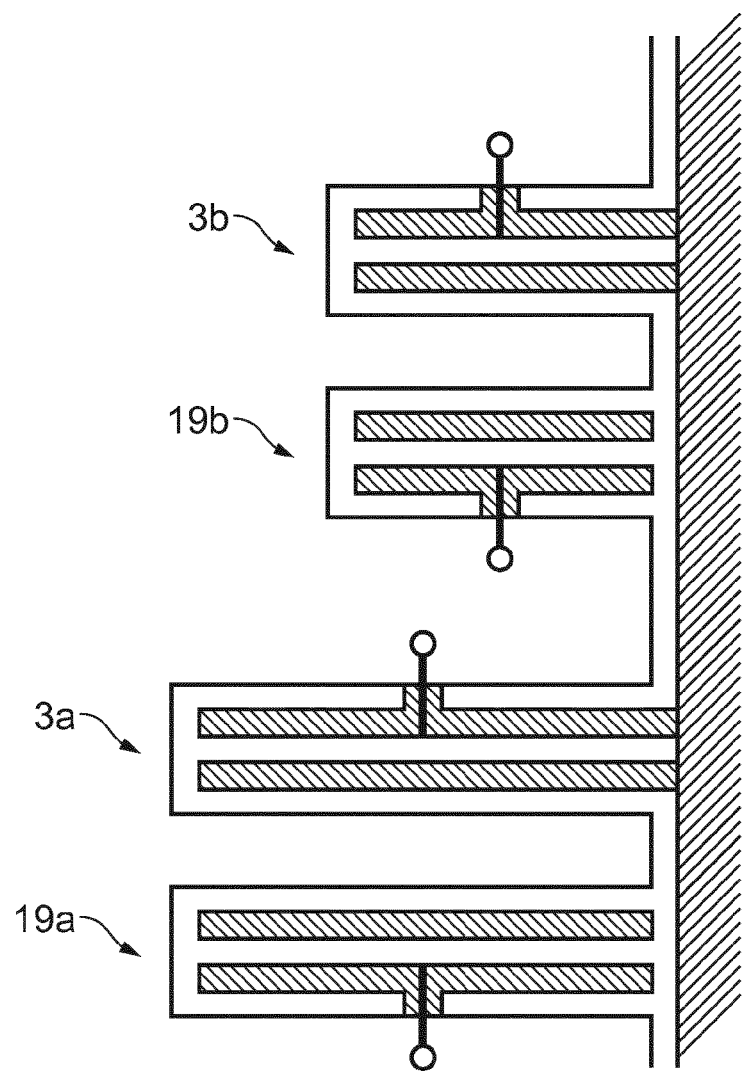
FIG. 9 is a schematic illustration of a system according to the invention comprising first and second measurement probes, and first and second temperature reference probes.

FIG. 9 discloses a system comprising a first measurement probe 3a and a second measurement probe 3b.

As discussed above, the resonance frequency of a coaxial probe is inverse proportional to its length. The length of the measurement probe 3a is $l_a$ and the length of the measurement probe 3b is $l_b$, where $l_b < l_a$.

For a certain erosion of $\Delta l$, the length of measurement probe 3a becomes $l_a - \Delta l$, and thus the resonance frequency of measurement probe 3a is:

$$f_1 \sim 1/(l_a - \Delta l) \qquad \text{[Equation 4]}$$

Likewise, the resonance frequency of measurement probe 3b is:

$$f_2 \sim 1/(l_b - \Delta l) \qquad \text{[Equation 5]}$$

The length $l_{a,b} - \Delta l$ is temperature dependent, but for $\Delta l \ll l_{a,b}$, only $l_{a,b}$ can be assumed to be temperature dependent: $l_{a,b}(T)$.

Consequently, the ratio $$\frac{f_2(l_b(T) - \Delta l)}{f_1(l_a(T) - \Delta l)} = \frac{l_a(T) - \Delta l}{l_b(T) - \Delta l} \qquad \text{[Equation 5]}$$

yields $$f_2(l_b(T) - \Delta l) = f_1(l_a(T) - \Delta l) \frac{l_a(T) - \Delta l}{l_b(T) - \Delta l} \qquad \text{[Equation 6]}$$

and the temperature dependence can be obtained from the temperature reference probes 19a and 19b, which are erosion independent due to its short circuits.

In the table below, the ratio of equation 5 is calculated for a set of erosions values Δl for measurement probes having lengths $l_a$=0.24 m and $l_b$=0.16 m.

| Δl (μm) | Ratio $\frac{l_a(T) - \Delta l}{l_b(T) - \Delta l}$ | $f_1$ (Δl) (MHz) | $f_2$ (Δl) (MHz) |
|---|---|---|---|
| 0 | 1.5 | 187 | 280.5 |
| 1 | 1.500003125019531 | 187.000779 | 280.501753 |
| 2 | 1.500006250078126 | 187.001558 | 280.503506 |
| 4 | 1.500012500312508 | 187.003116 | 280.507012 |
| 8 | 1.500025001250062 | 187.006233 | 280.514025 |
| 12 | 1.500037502812711 | 187.009350 | 280.521039 |

As can be seen from the table, erosion makes the resonance frequency increase. For example, an erosion of Δl=1 μm in probe 3a makes the resonance frequency increase by 779 Hz in resonator 1, and for resonator 2 the same erosion makes the resonance increase by 1.753 kHz. Also, as is evident from the Ratio column, the larger difference in lengths $l_a$ and $l_b$, the better erosion accuracy is obtained. Assuming that temperature induced elongation/contraction is monitored accurately, a high degree of erosion accuracy, e.g. in the order of 1 μm, is obtainable.

The system may also comprise a first temperature reference probe 19a and a second temperature reference probe 19b, as is disclosed in FIG. 9. The first temperature reference probe 19a has the same physical dimensions as the first measurement probe 3a. Likewise, the second temperature reference probe 19b has the same physical dimensions as the second measurement probe 3b. The temperature reference probes 19a and 19b are arranged to compensate for temperature expansion of the measurement probes 3a and 3b, respectively, in the same way as has been discussed above. Consequently, by incorporating the temperature reference probes 19a and 19b into the system, the signals measured by the probes 3a, 3b can be compensated for temperature as well as for erosion induced length variations of the measurement probes 3a, 3b.

According to an alternative erosion compensation scheme, at least two open-ended probes having different inner and outer coaxial diameters are employed. The different inner and outer coaxial diameters will result in different penetration depths of the electromagnetic field emerging from the probes. According to this scheme, the unknown length $l=l_t-\Delta l$ is treated in the same way as other unknown variables and, consequently, is calculated in the same way as other unknown variables. A necessary condition for this scheme to work is that the system needs to have a sufficient numbers of probes with different penetration depth such that the values for all unknown variables can be solved simultaneously.

A typical scheme for solving the values for the unknown variables may advantageously involve regularization methods, e.g. Tikhonov regularization. These methods are known as such and will not be discussed at any length here. However, a typical method of using a radio frequency model in combination with a gradient-like iterative algorithm to extract unknown parameter values may comprise the following steps.

First, the reflection coefficient of a probe according to the invention is defined as:

$$S_{11} = \Gamma = \frac{Z_{tot} - Z_c}{Z_{tot} + Z_c} \quad \text{[Equation 7]}$$

where $Z_{tot}$ is the input impedance looking into the measurement reference plane, and $Z_c$ is the characteristic impedance of the measurement system (N.B. not the characteristic impedance of the probe).

Assuming there is a plurality of known parameters, e.g.
T: temperature
P: pressure
f: frequency
and a plurality of unknown parameters, e.g.
s: salinity
d: liquid film thickness
n: gas condensate/H2O volume fraction
m: hydrocarbon gas/H2O steam volume fraction
length: length of the measurement probe (due to erosion)
the next step is to minimise the following function:

$$J(s, d, n, m) = \quad \text{[Equation 8]}$$
$$\frac{1}{2}\int_{\omega 1}^{\omega 2} \left(S_{11}^1(s, d, n, m, \text{length}, \omega') - \tilde{S}_{11}^1(\omega')\right)^2 d\omega +$$
$$\frac{1}{2}\int_{\omega 1}^{\omega 2} \left(S_{11}^2(s, d, n, m, \text{length}, \omega') - \tilde{S}_{11}^2(\omega')\right)^2 d\omega + \ldots +$$
$$\frac{1}{2}\alpha_1(s-s_0)^2 + \frac{1}{2}\alpha_2(d-d_0)^2 + \frac{1}{2}\alpha_3(n-n_0)^2 +$$
$$\frac{1}{2}\alpha_4(m-m_0)^2 + \frac{1}{2}\alpha_5(\text{length}-\text{length}_0)^2 + \ldots$$

In this function, $\alpha_n$ are the Tikhonov regularization parameters, which are $0<\alpha_n<1$, $S_{11}^1(s,d,n,m,\omega')$ is the reflexion coefficient model expression, and $\tilde{S}_{11}^1(\omega')$ is the measured response measured as a function of the frequency only.

It is to be noted that more terms can be added to the above functional equation, where these added terms may represent any sensor model for any arbitrary sensor. The above equation may be solved by a gradient like method so that, eventually, the values of all unknown parameters are extracted.

Figures 10, 11:
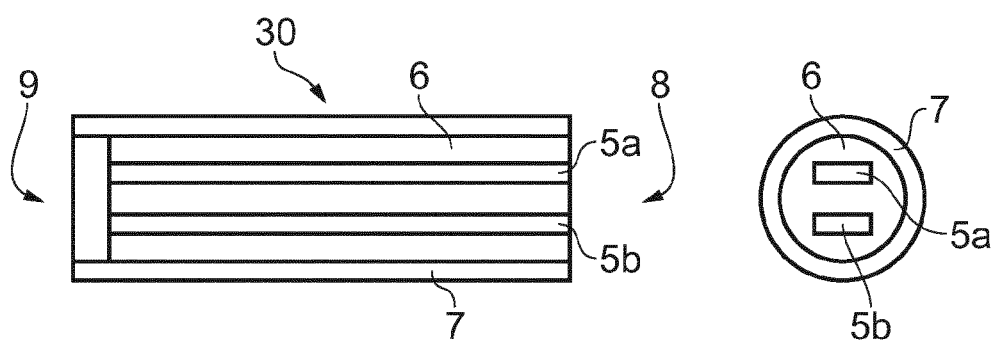
FIG. 10 is a schematic illustration of a measurement probe according to a third embodiment of the invention.
FIG. 11 is a front view of the measurement probe according to FIG. 10.

FIGS. 10 and 11 disclose another embodiment of a measurement probe 30 according to the invention. The measurement probe 30 comprises an outer probe shield 7 and a dielectric insulator 6. However, in this case the measurement probe 30 comprises an inner, first probe conductor 5a and an inner, second probe conductor 5b. At the first terminal 8 the probe 30 is open-ended, and at the second terminal 9 the probe shield 7 and the probe conductors 5a, 5b are electrically connected. Consequently, the probe 30 operates as an open-ended quarter-wave probe in the same way as the above-discussed probe 3. The probe conductors 5a, 5b may be connected to the signal processor 4 directly. Alternatively, the conductors may be connected to a balun (not disclosed) which, in turn, is connected to the signal processor 4.

Figure 12:
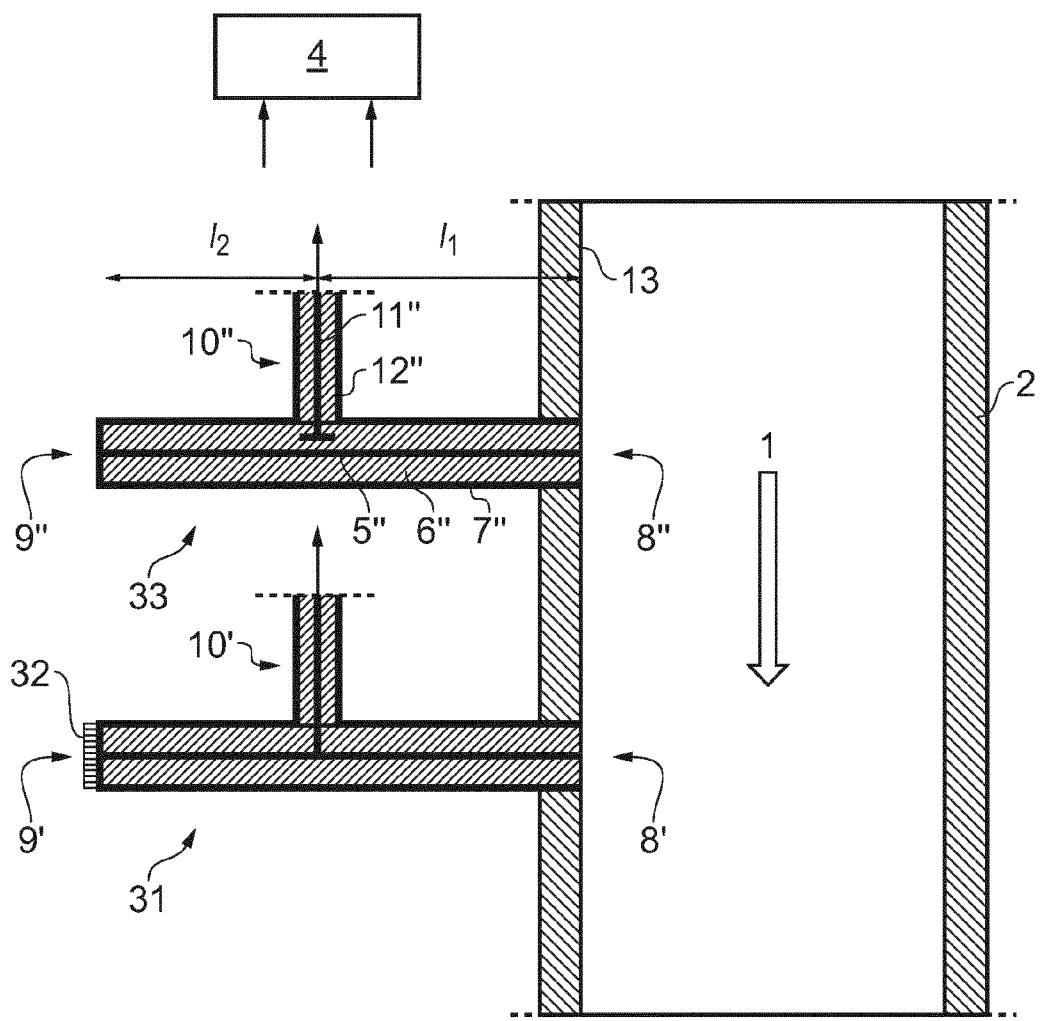
FIG. 12 is a schematic illustration of measurement probes according to fourth and fifth embodiments of the invention.

FIG. 12 discloses further embodiments of measuring probes which may be used in a system according to the invention. In particular, figure discloses a first measurement probe 31 which is connected to the signal processor 4 via a signal conduit 10'. The probe 31 is identical to the probe 3 disclosed in FIG. 1 except that the second terminal 9' of the probe 31 is not short-circuited at the second terminal 9' but comprises a resistive element 32, e.g. a resistor, providing a pre-determined impedance between the probe conductor 5' and the probe shield conductor 7'. The figure also discloses a second measurement probe 33 which is generally identical to the probe 3 disclosed in FIG. 1. However, the probe 33 is connected to the signal processor not galvanically but capacitively, i.e. via a capacitive coupling arranged between probe conductor 5" and the signal line conductor 11" of the signal line 10".

Simulations has revealed that it may be advantageous to use different types of measurement probes to measure different types of fluid characteristics, and also that it may be advantageous to use different types of measurement probes to measure different parameter ranges for a specific parameter. In the following, this will be discussed in more detail with reference to FIGS. 13-35, in which the measurement probes disclosed in FIGS. 1 and 12 are simulated to be subjected to air and saline water.

In the simulations, the probes 3, 31 and 33 were assumed to be coaxial probes having a length of 260 mm, a coaxial outer diameter of 10 mm and a coaxial inner diameter of 5 mm. The signal lines 10, 10' and 10", respectively, were simulated to be connected to the probes 3, 31 and 33 in between the first and second terminals, i.e. such that $l_1=l_2$. For simulating the dielectric properties of the saline water, a saline water model based on Gadani et al. (*Effect of salinity on the dielectric properties of water*, D H Gadani et al., Indian Journal of Pure & Applied Physics, Vol. 50, June 2012, pp. 405-410) was used. For simulating the signal in the probes 3, 31, 33, a quasi-static model as disclosed in *Static Analysis of an Open Ended Coaxial Line Terminated by Layered Media*, SIQI FAN et al., IEEE Transactions on instrumentation and measurement. VOL. 39, No. 2, April 1990, pp. 435-437, was employed. In the simulations, the relative complex permittivity of the probe insulators was set to 10-0.00001i, and the conductivity of probe conductors was set to $1.6*10^7$ S/m. For the resistive element 32 of probe 31, a resistive value of 1 ohm was used. For the capacitive coupling between probe the conductor 5" and the signal line conductor 11" of probe 33, a coupling capacitance of 5 pF was used.

Figure 13:
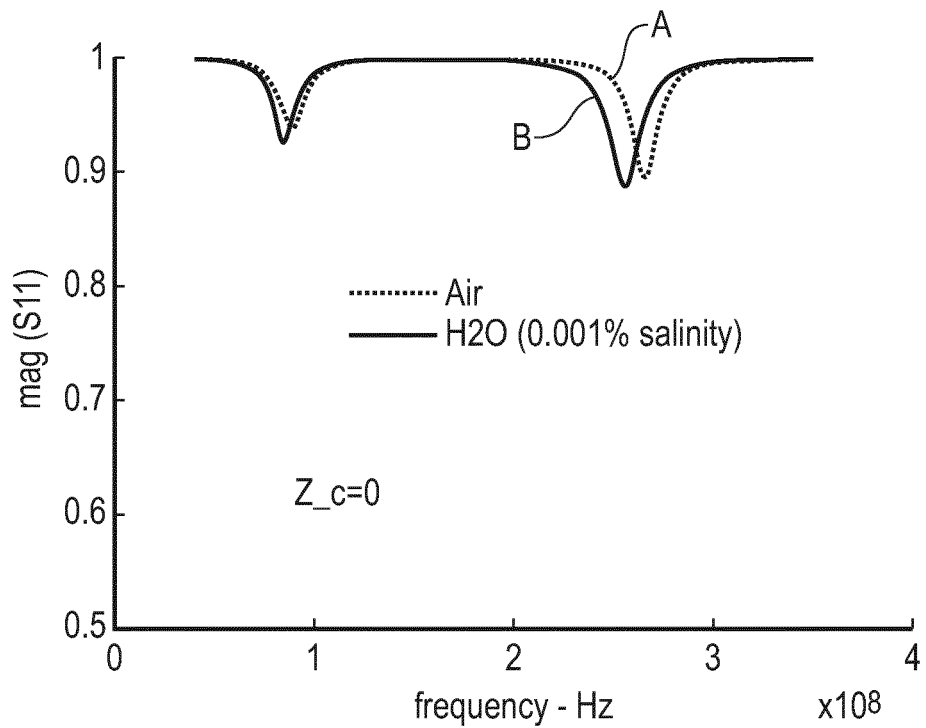
Figure 14:
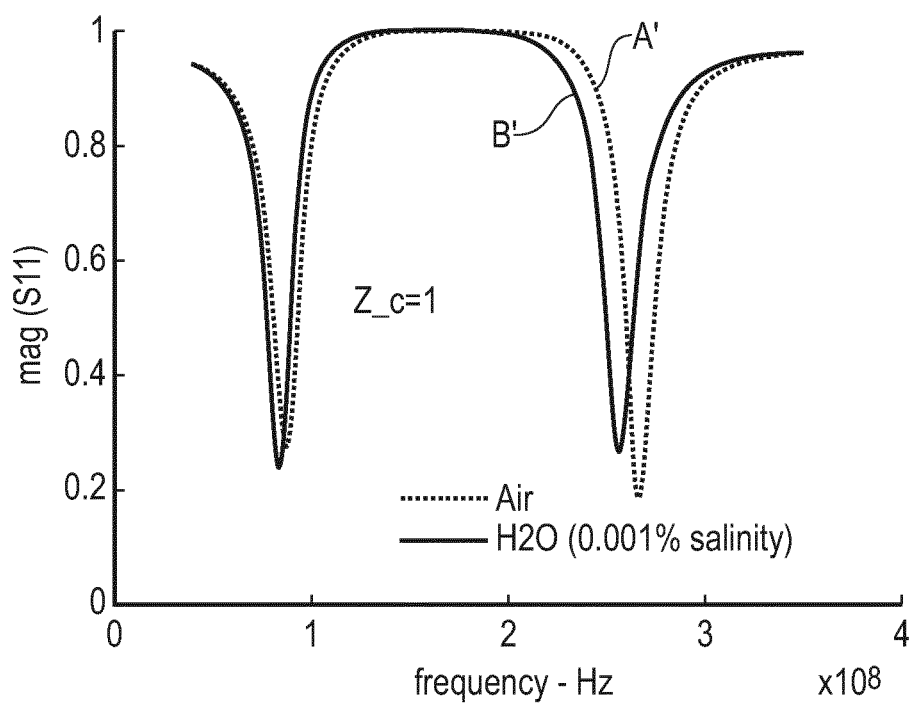

FIG. 13 illustrates simulated reflection signals A and B for the first probe 3, i.e. the probe having a short-circuited second terminal 8 in FIG. 1. Signal A represents the reflected signal when the fluid at the first terminal is air, and the second signal B represents the reflected signal when the fluid is water having a salinity of 0.001%. FIG. 14 illustrates corresponding simulated reflection signals A' and B' for the probe 31, i.e. the probe in FIG. 12 in which the second terminal 9' comprises a resistive element 32 providing a pre-determined impedance between the probe conductor 5' and the probe shield conductor 7'.

In FIGS. 13-35, the parameter on the x-axis is the frequency of the reflected signal, and the parameter on the y-axis is the magnitude of the reflection coefficient S11.

FIG. 13 discloses the two lowest resonance poles of the reflection signals A and B—a first pole at approximately 80 MHz and a second pole at approximately 260 MHz. As is evident from FIG. 13, changing the fluid from air to water having a salinity content of 0.001% will cause the frequencies of the resonance poles to shift. However, the magnitude of the signals at the resonance poles, as indicated by the mag(S11) parameter, are not particularly large.

As is evident from FIG. 14, changing the fluid from air to water having a salinity of 0.001% will cause the frequencies of the resonance poles to shift also in the signals of probe 31. However, as compared to the signals of probe 3, the magnitude of the signals A' and B' at the resonance poles are much more predominant and, therefore, easier to detect. In other words, the reflection signals of probe 3, i.e. the probe having a short-circuited second terminal 9, shows much less distinctive resonance poles than the reflection signals of probe 31, i.e. the probe having a 1 ohm resistance loading the second terminal 9'. Consequently, shifts in resonance pole frequency are more easily detected using probe 31 and, since resonance pole frequency shifts are typically due to changes in the water content of the fluid, it can be concluded that probe 31 is more suitable for detecting water content variations than probe 3.

Figure 15:
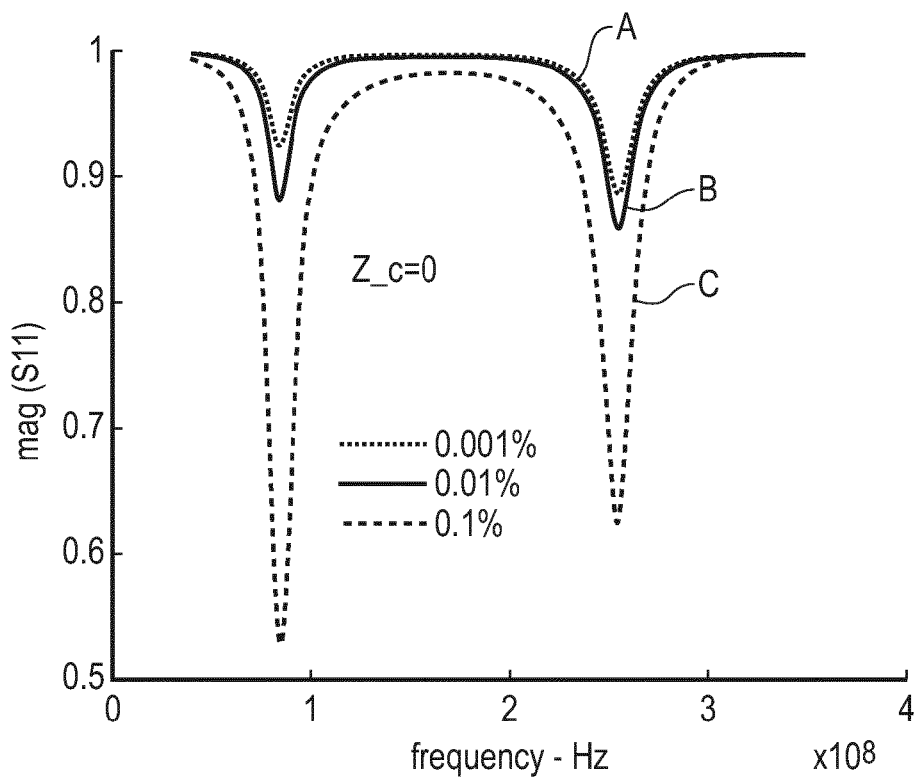
Figure 16:
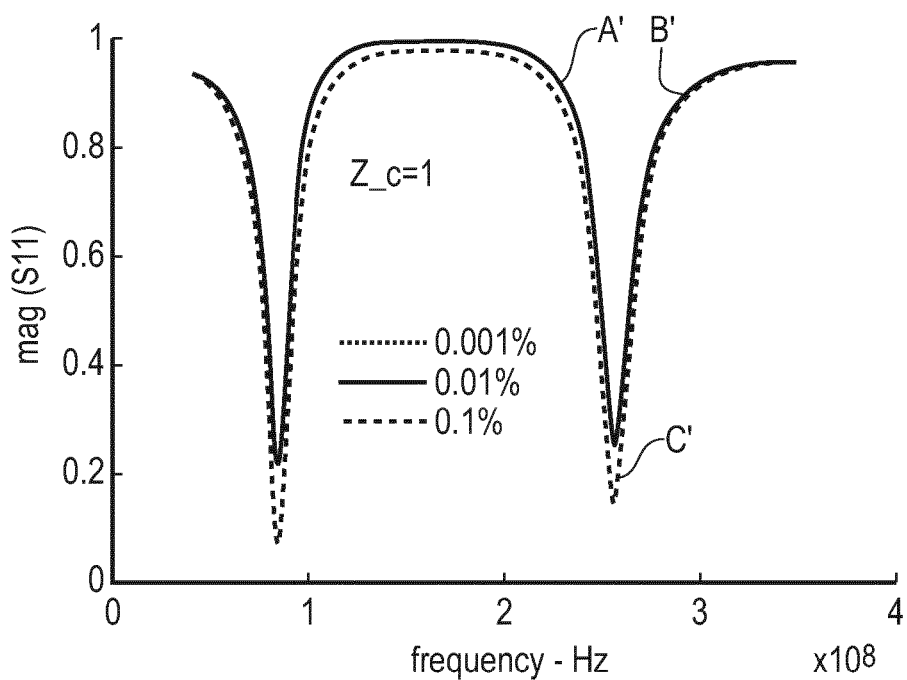

FIG. 15 illustrates another set of simulated reflection signals A, B and C for probe 3. In this case, signal A represents the reflected signal when the fluid at the first terminal is water having a salinity of 0.001%, signal B represents the reflected signal when the fluid is water having a salinity of 0.01%, and signal C represents the reflected signal when the fluid is water having a salinity of 0.1%. FIG. 16 illustrates corresponding simulated reflection signals A', B' and C' for probe 31.

As is evident from FIGS. 15 and 16, variations in the salinity of the fluid within the range of 0.001%-0.1% will not cause any significant shift of the resonance pole frequencies. However, for both probes 3 and 31 the amplitude of the signals at the resonance poles will increase as salinity increases, although probe 3 is more sensitive to salinity variations than probe 31. On the other hand, probe 31 shows significantly larger amplitude for all three salinity levels, which makes probe 31 more useful for tunability—i.e. probe 31 is better suited for detecting resonance pole frequency shifts when the salinity is relatively low or zero.

The table in FIG. 17 summarises the resonance pole amplitude values of the simulations disclosed in FIGS. 15 and 16.

Figure 18:
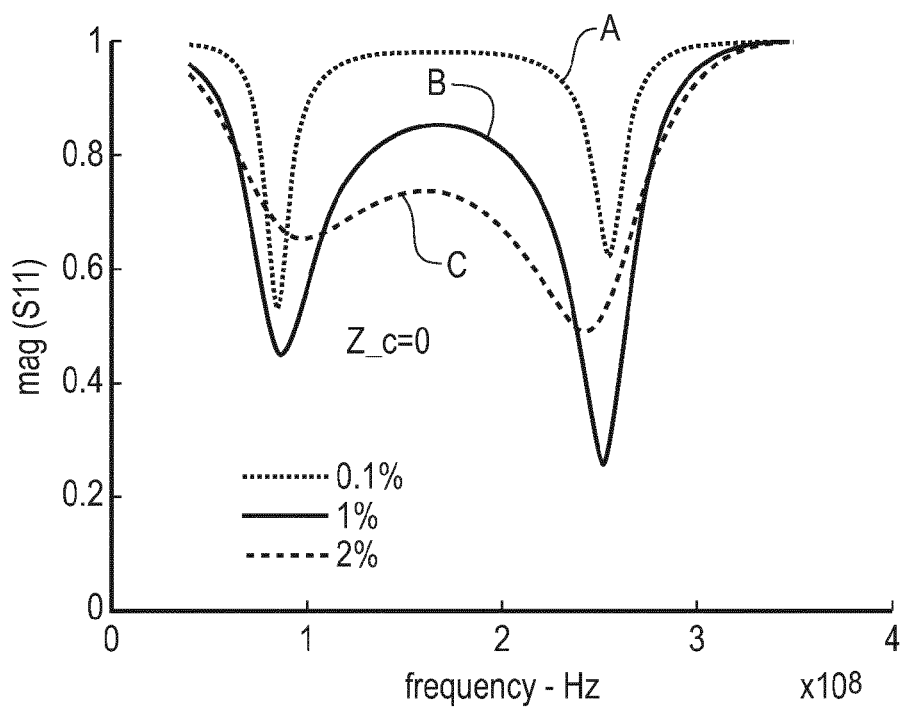
Figure 19:
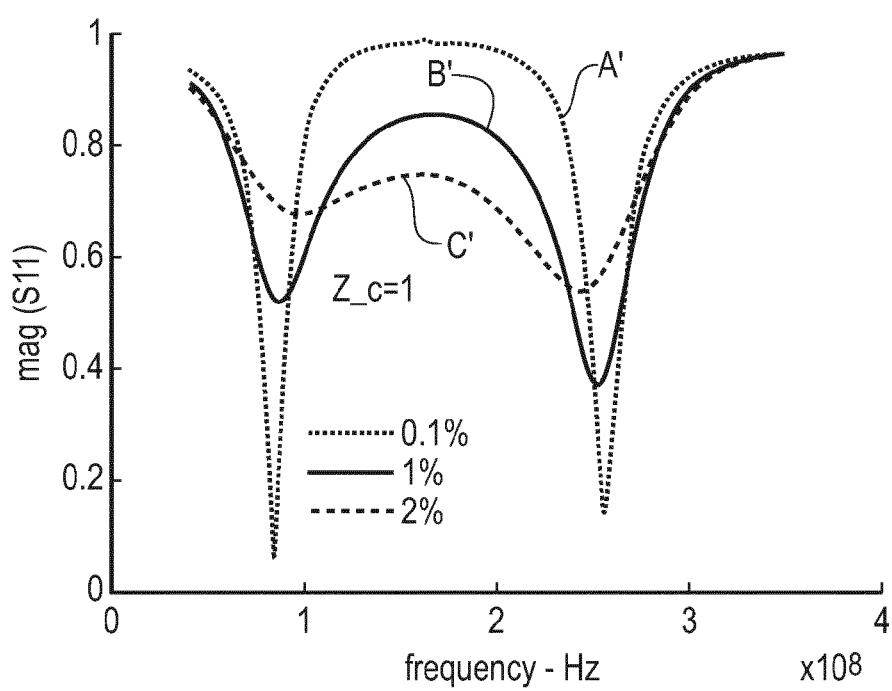

FIG. 18 illustrates yet another set of simulated reflection signals A, B and C for probe 3. In this case, signal A represents the reflected signal when the fluid at the first terminal is water having a salinity of 0.1%, signal B represents the reflected signal when the fluid is water having a salinity of 1%, and signal C represents the reflected signal when the fluid is water having a salinity of 2%. FIG. 19 illustrates corresponding simulated reflection signals A', B' and C' for probe 31.

Within the salinity interval of 0.1%-1%, probe 31 is more sensitive for salinity variations than probe 3. Also, for probe 3 the mag(S11) parameter value does not change monotonically for the three salinity levels, whereas it does for probe 31. Thus, there is a stagnation point in this salinity interval where the sensitivity of probe 3 is poor.

Figure 20:
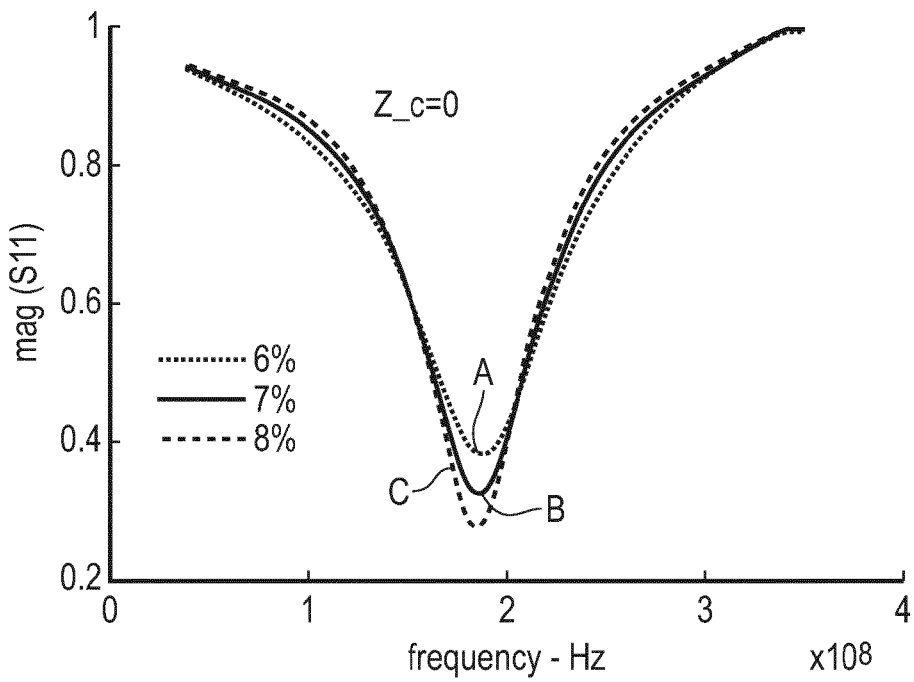

FIG. 20 illustrates yet another set of simulated reflection signals A, B and C for probe 3. In this case, signal A represents the reflected signal when the fluid at the first terminal is water having a salinity of 6%, signal B represents the reflected signal when the fluid is water having a salinity of 7%, and signal C represents the reflected signal when the fluid is water having a salinity of 8%. FIG. 20 illustrates corresponding simulated reflection signals A', B' and C' for probe 31.

Figure 21:
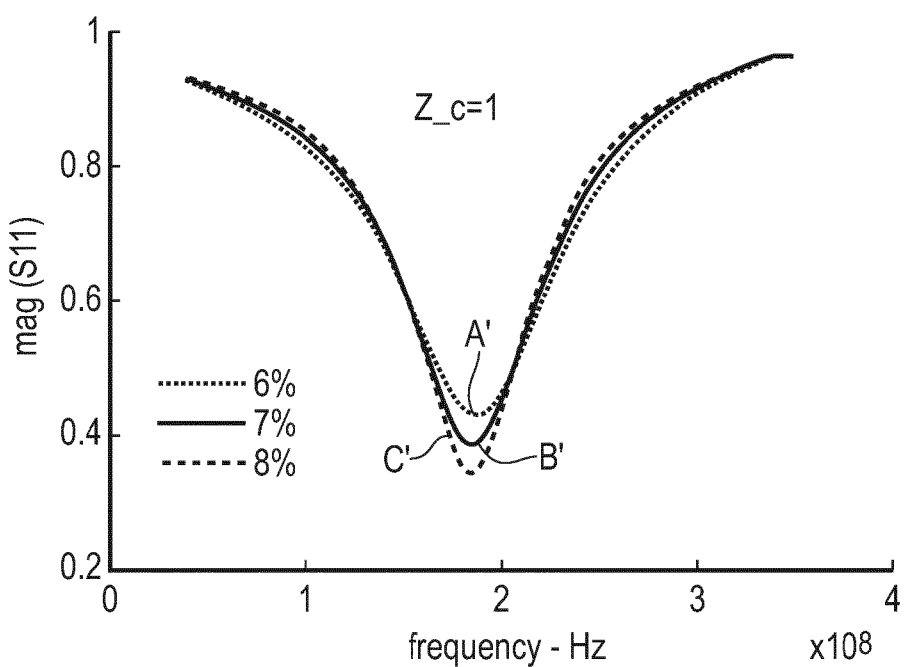

As is evident from FIGS. 20 and 21, the reflection response of both probes 3 and 31 display only one resonance pole at approximately 185 MHz. Consequently, when the salinity of the water exceeds approximately 3%, the reflection response of the probes transform from having a characteristic of a quarter-wave resonator to that of a half-wave resonator. This is due to the water becoming more conductive and loading the open-ended terminals 8, 8' of the probes 3, 31 with a "low" resistive value.

The table in FIG. 22 summarises the resonance pole amplitude values of the simulations disclosed in FIGS. 20 and 21.

Figure 23:
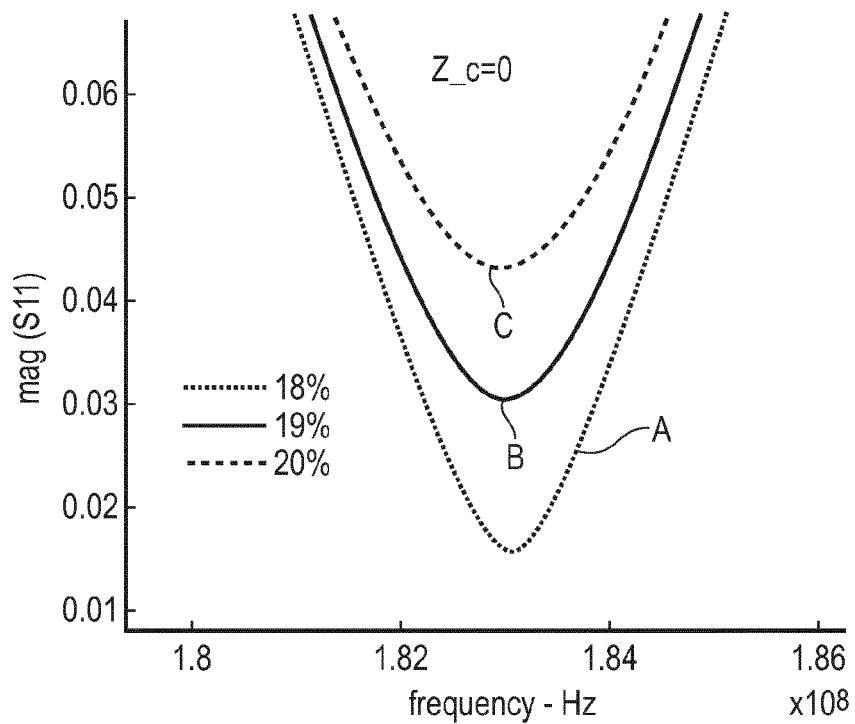
Figure 24:
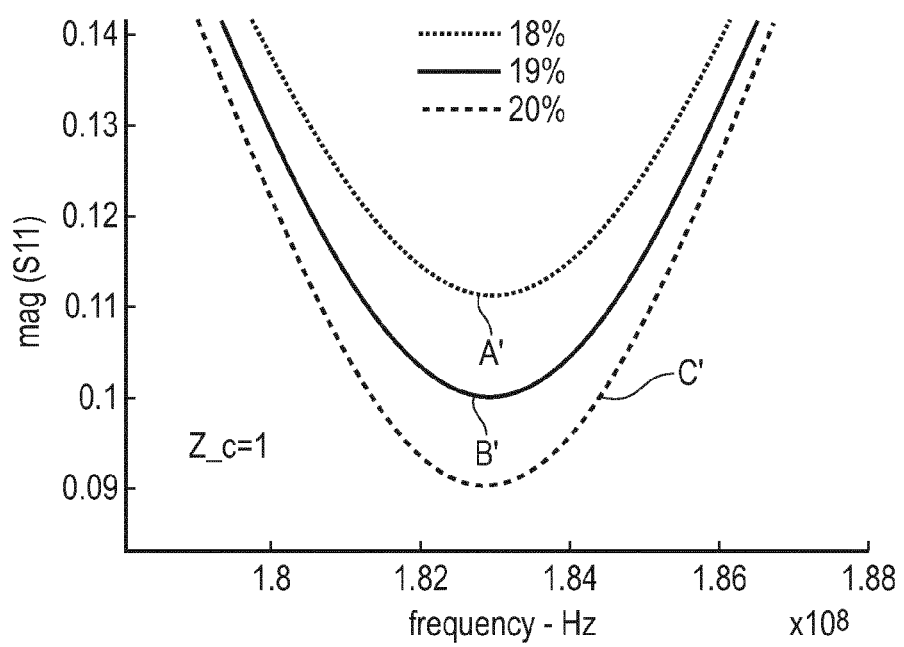

FIG. 23 illustrates another set of simulated reflection signals A, B and C for probe 3. In this case, signal A represents the reflected signal when the fluid at the first terminal is water having a salinity of 18%, signal B represents the reflected signal when the fluid is water having a salinity of 19%, and signal C represents the reflected signal when the fluid is water having a salinity of 20%. FIG. 24 illustrates corresponding simulated reflection signals A, B and C for probe 31.

Even though general sensitivity is small for both probes 3, 31 in this salinity inteval, it is noticed that resonance pole amplitude for probe 3 is monotonically lifted upwards for increased salinity, while for probe 31, it is monotonically lowered downwards. Consequently, the pole amplitude of probe 3 has a turning point between 8% and 18% salinity where sensitivity of the probe is poor if not zero, while the resonance pole amplitude of probe 31 is a monononic function from 6% salinity to 20% salinity.

Figure 25:
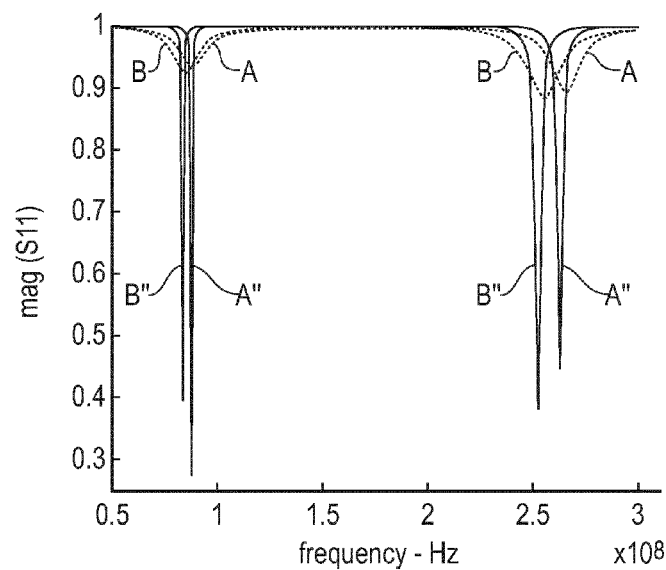

FIG. 25 illustrates simulated reflection signals A and B for probe 3, i.e. the probe in which the probe conductor is galvanically connected to the signal line conductor 11. Signal A represents the reflected signal when the fluid at the first terminal 8 is air, and the second signal B represents the reflected signal when the fluid is water having a salinity of 0.001%. FIG. 25 also illustrates simulated reflection signals A" and B" for probe 33, i.e. the probe in which the probe conductor 5" is capacatively connected to the signal line conductor 11". Again, signal A" represents the reflected signal when the fluid at the first terminal 8" is air, and the second signal B" represents the reflected signal when the fluid is water having a salinity of 0.001%.

Figure 26:
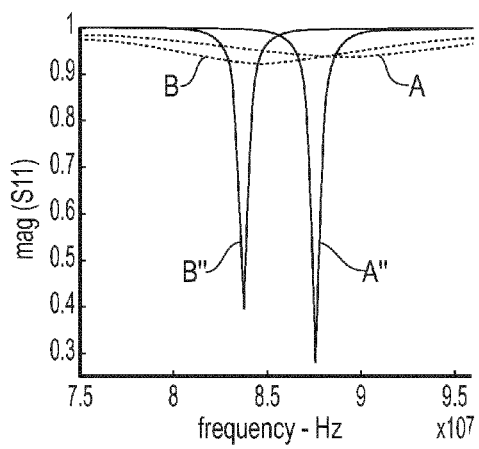
Figure 27:
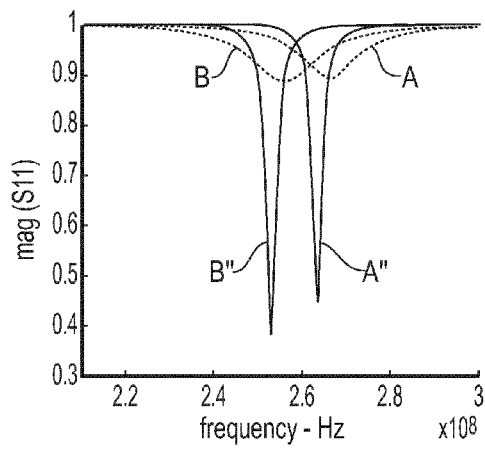

In FIG. 25, the two lowest resonance poles of the signals A, B, A" and B" are displayed—a first pole at approximately 85 MHz and a second pole at approximately 260 MHz. This is due to the open-ended first terminals 8, 8" and the short-circuited second terminals 9, 9", which make the probes act as quarter-wave resonators. FIGS. 26 and 27 are zoomed-in views of the pole regions.

As is evident from FIGS. 25-27, the signals A" and B" rendered by the capacitively connected probe, i.e. probe 33, are more distinct than the signals A and B rendered by the galvanically connected probe, i.e. probe 3, in that the signals A" and B" have sharper edges or flanks. Consequently, the capacitively connected probe gives better sensitivity when detecting frequency shift as compared to the galvanically connected probe. Consequently, shifts in resonance pole frequency are more easily detected using probe 33 than probe 3 and, since resonance pole frequency shifts are typically due to changes in the water content of the fluid, it can be concluded that probe 33 is more suitable to detect water content variations than probe 3, at least for water having low salinity levels.

Figure 28:
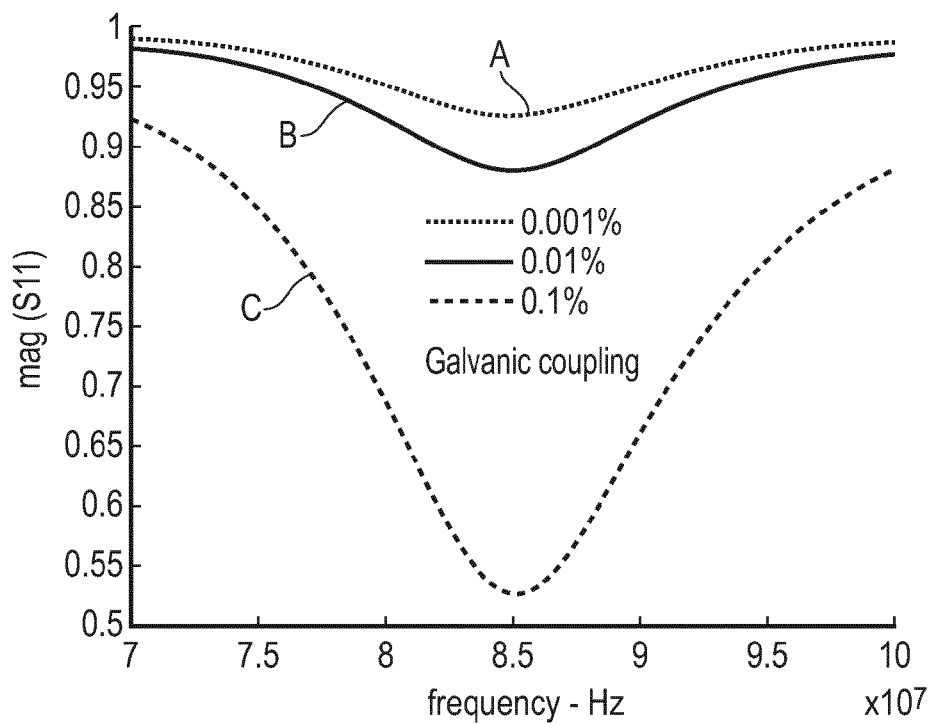
Figure 29:
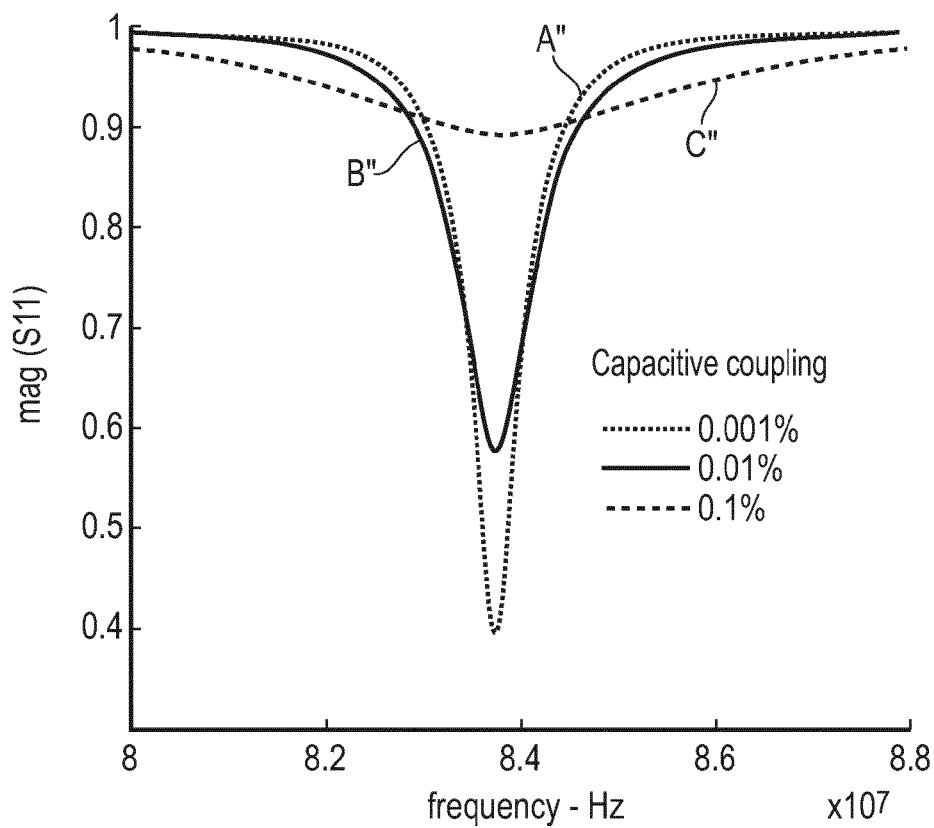

FIG. 28 illustrates another set of simulated reflection signals A, B and C for probe 3. In this case, signal A represents the reflected signal when the fluid at the first terminal is water having a salinity of 0.001%, signal B represents the reflected signal when the fluid is water having a salinity of 0.01%, and signal C represents the reflected signal when the fluid is water having a salinity of 0.1%. FIG. 29 illustrates corresponding simulated reflection signals A", B" and C" for the second probe 33. In FIGS. 28 and 29 only the first resonance pole is disclosed.

FIGS. 28 and 29 disclose that, for the capacitively connected probe 33, a change in salinity from 0.001% to 0.01% will bring about an increase in the mag(S11) parameter value of approximately 0.2, and a change in salinity from 0.01% to 0.1% will bring about a further increase of approximately 0.3. However, for the galvanically connected probe 3, the change in salinity from 0.001% to 0.01% will bring about a decrease in the mag(S11) parameter value of approximately 0.05, and a change in salinity from 0.01% to 0.1% will bring about a further decrease of approximately 0.37. Consequently, in the salinity range of 0.001% to 0.01% the capacitively coupled probe 33 is approximately 4 times more sensitive than the galvanically coupled probe 3, whereas in the salinity range of 0.01% to 0.1%, the galvanically coupled probe 3 is approximately 1.23 times more sensitive than the capacitively coupled probe 33. Thus, in the salinity range of 0.001% to 0.1% it may be advantageous to use both a capacitively coupled and a galvanically coupled probe.

Figure 30:
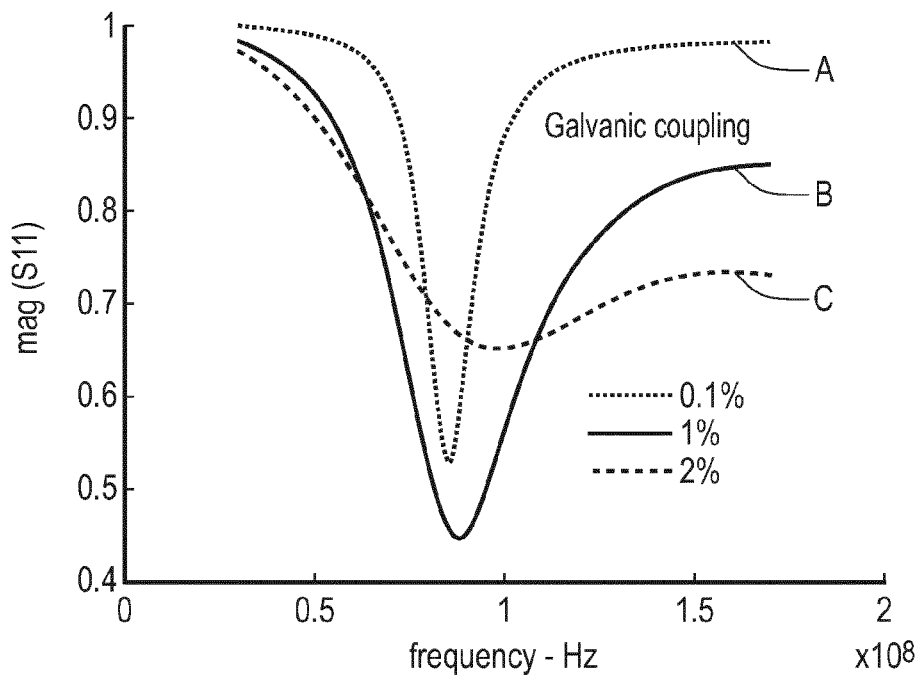
Figure 31:
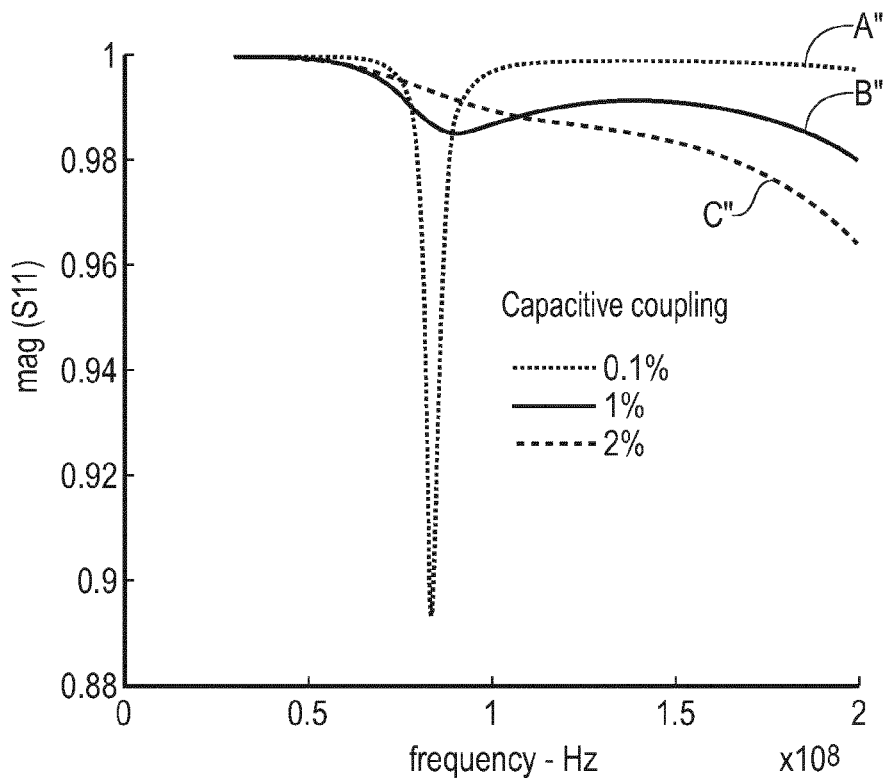

FIG. 30 illustrates yet another set of simulated reflection signals A, B and C for probe 3. In this case, signal A represents the reflected signal when the fluid at the first terminal is water having a salinity of 0.1%, signal B represents the reflected signal when the fluid is water having a salinity of 1%, and signal C represents the reflected signal when the fluid is water having a salinity of 2%. FIG. 31 illustrates corresponding simulated reflection signals A", B" and C" for probe 33.

When increasing the salinity in the salinity interval of 0.1%-2%, the signal of the capacitively coupled probe, i.e. probe 33, renders a monotonically increasing mag(S11) parameter value at the first pole, i.e. the pole having the lowest frequency value. The galvanically coupled probe, on the other hand, has a stagnation point between 1% and 2% salinity. However, when the salinity increases from 1% to 2%, the change in the mag(S11) parameter value of the capacatively coupled probe is significantly smaller (<0.02) than the corresponding value of the galvanically coupled probe (close to 0.2).

Figure 32:
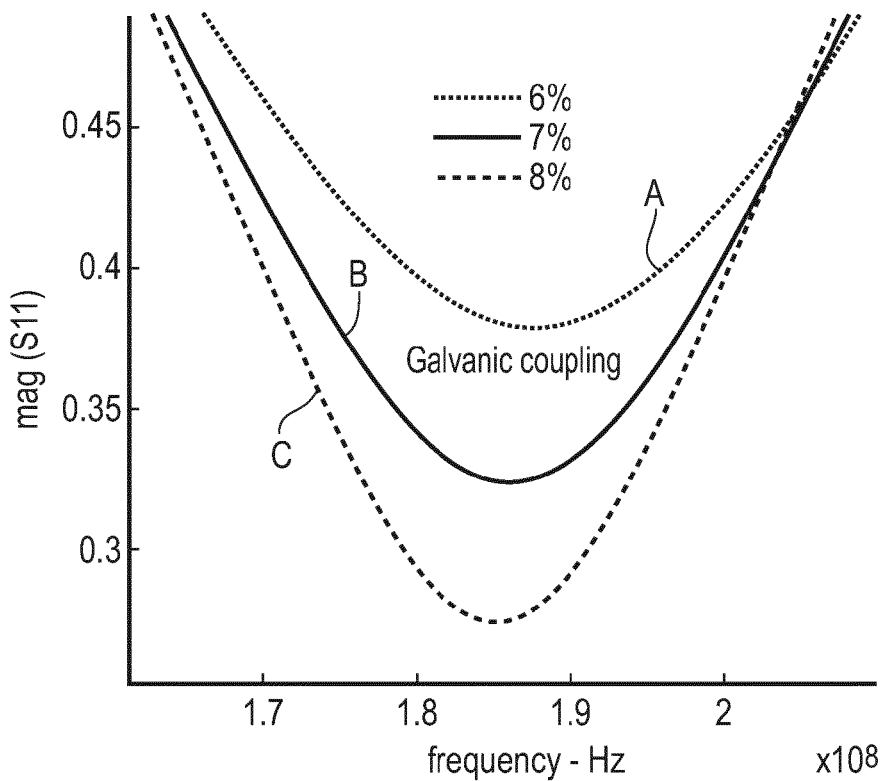

Due to the stagnation point, there is a salinity value between 1% and 2% salinity where the galvanically coupled probe is insensitive to salinity variations. The signal of the capacitively coupled probe has no stagnation point in this range and, thus, there is no salinity point where the sensitivity of the capacitively coupled probe is zero. However, in regions outside the stagnation point, the galvanically coupled probe is approximately 10 times more sensitive than the capacitively coupled probe. It is thus advantageous to use both probes to cover the entire range from 0.1% to 2% salinity FIG. 32 illustrates a further set of simulated reflection signals A, B and C for the galvanically coupled probe 3. In this case, signal A represents the reflected signal when the fluid at the first terminal is water having a salinity of 6%, signal B represents the reflected signal when the fluid is water having a salinity of 7%, and signal C represents the reflected signal when the fluid is water having a salinity of 8%. FIG. 22 illustrates corresponding simulated reflection signals A", B" and C" for the capacitively coupled probe 33.

Figure 33:
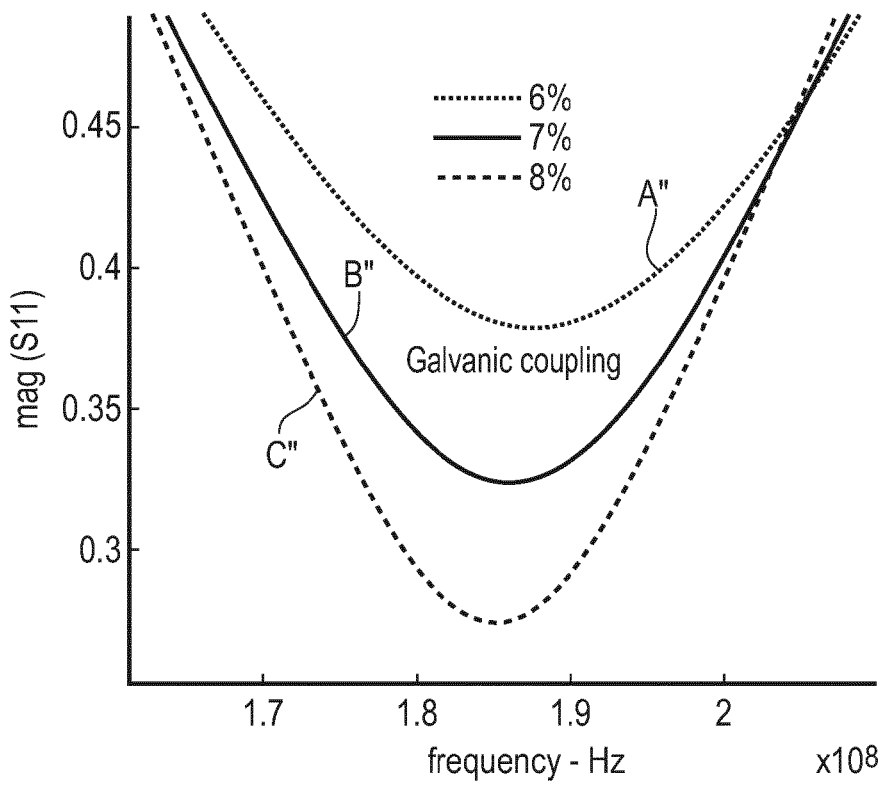

As is evident from FIGS. 32 and 33, the galvanically coupled probe 33 offers approximately 6.2 times better salinity sensitivity than the capacitive coupled probe 3 in the salinity range of 6% to 8%.

Figure 34:
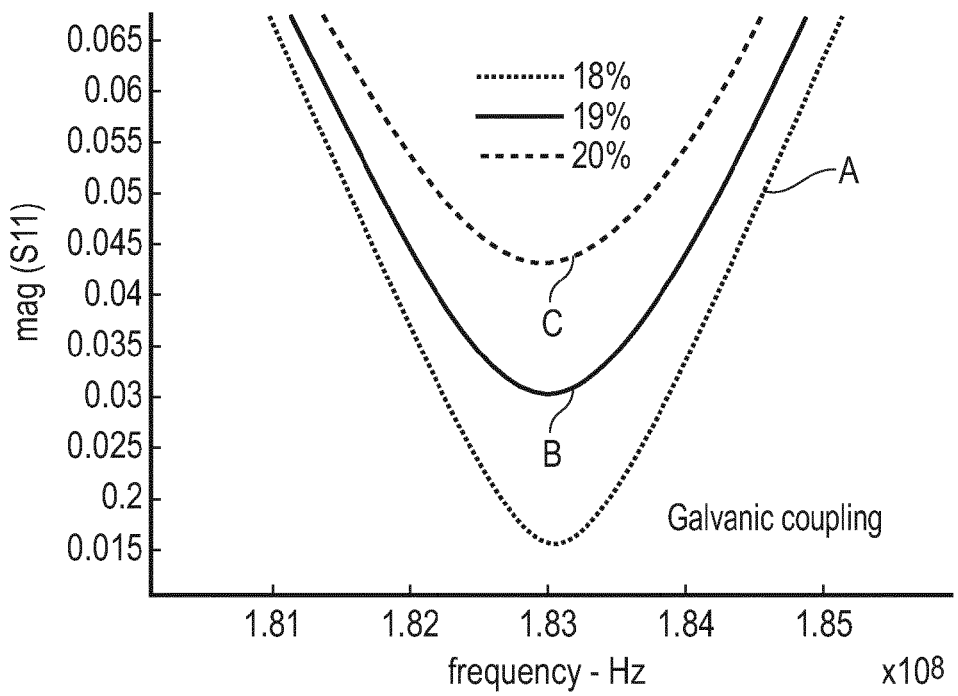
Figure 35:
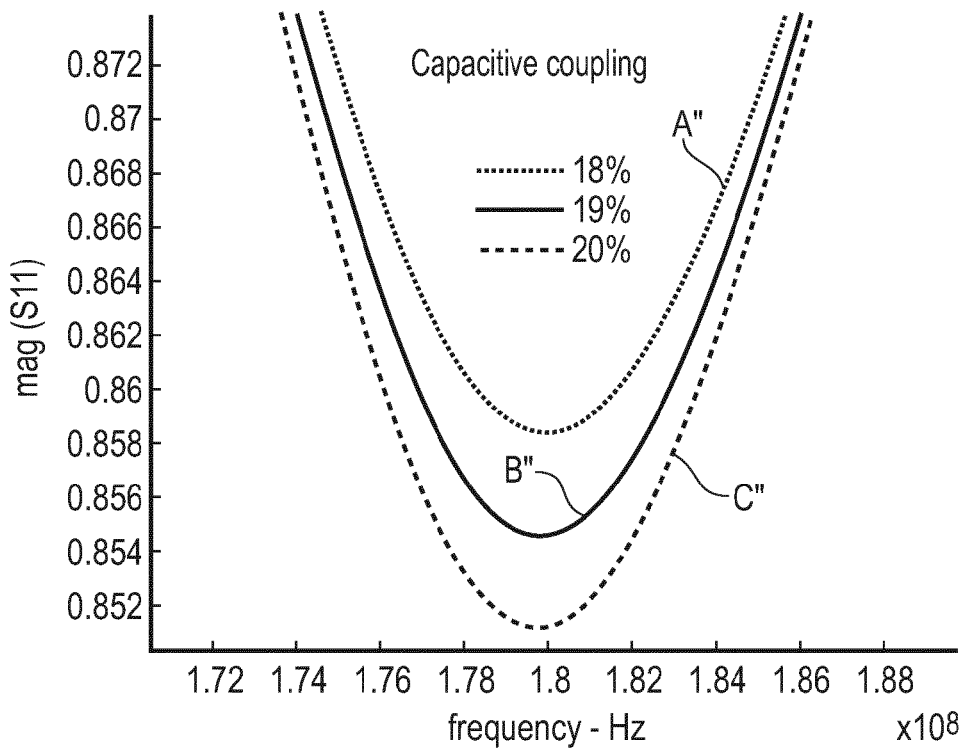

FIG. 34 illustrates a further set of simulated reflection signals A, B and C for the galvanically coupled probe 3. In this case, signal A represents the reflected signal when the fluid at the first terminal is water having a salinity of 18%, signal B represents the reflected signal when the fluid is water having a salinity of 19%, and signal C represents the reflected signal when the fluid is water having a salinity of 20%. FIG. 35 illustrates corresponding simulated reflection signals A", B" and C" for the capacitively coupled probe 33.

Within the salinity range of 6% to 8%, the signal of the galvanically coupled probe 3 has a stagnation point between 8% and 18% salinity, where salinity sensitivity is poor if not zero. However, the signal of the capacitively coupled probe 33 is changing monotonically, even though with significantly smaller amplitude changes as compared to the signal of the the galvanically coupled probe 3.

The above-discussed simulations demonstrate that in a system according to the invention, the at least one measurement probe to be used should be adapted to the parameter type and parameter range to be monitored. Also, the simulations demonstrate that it may be advantageous to include a plurality of measurement probes into the system in order to more accurately measure a plurality of parameter types and parameter ranges.

In particular, if water content and/or water salinity is to be measured, it may be advantageous to combine, in the system, the above-disclosed probe 3 with at least one of the above-disclosed probes 31 and 33. This demonstrates that the combination of the two probes 3, 31 overall increases salinity sensitivity and frequency sensitivity at least for the conditions and ranges presented here.

In the preceding description, various aspects of the invention have been described with reference to illustrative embodiments. However, the description is not intended to be construed in a limiting sense. Various modifications and variations of the illustrative embodiments which are apparent to persons skilled in the art to which the disclosed subject matter pertains, are deemed to lie within the scope of following claims.

The invention claimed is:

1. A system for determining at least one parameter of a multiphase fluid comprising hydrocarbons flowing in a conduit of a hydrocarbon processing facility, which system comprises:
    said conduit;
    at least one measurement probe which comprises:
        at least one probe conductor,
        a dielectric insulator arranged outside of the at least one probe conductor, and
        a probe shield arranged outside of the dielectric insulator;
    said at least one measurement probe being mounted to the conduit for measuring impedance signals indicative of at least one physical property of the fluid and further comprising a first, open-ended terminal where the at least one probe conductor, the dielectric insulator and the probe shield are coplanar and exposed to the flowing fluid when the system is in operation, wherein said physical property of the fluid influences the impedance of the first terminal of the at least one probe conductor; and
    a signal processor for interpreting the impedance signals to determine the at least one parameter;
    wherein the at least one measurement probe further comprises a second terminal, and the system comprises a signal line for conveying the impedance signals from the at least one measurement probe to the signal processor, said signal line being connected to the at least one measurement probe at a predetermined position between the first terminal and the second terminal;
    wherein said at least one parameter comprises any one of a flow rate of the fluid, a volume fraction of the fluid, a thickness of a liquid layer or film covering an inside wall of the conduit, and a composition of the liquid layer and/or film.

2. The system according to claim 1, wherein the signal line comprises:
    a signal conductor which is electrically connected to the at least one probe conductor at said predetermined position; and
    a signal shield which is electrically connected to the probe shield at said predetermined position.

3. The system according to claim 1, wherein the at least one measurement probe is mounted to the conduit such that the first terminal is coplanar with an inner side wall of the conduit.

4. The system according to claim 1, wherein the at least one probe conductor and the probe shield are electrically connected to each other at the second terminal such that the second terminal is short-circuited.

5. The system according to claim 4, wherein the predetermined position is located within a distance from the middle of the at least one measurement probe of from 10%-20% of the length of the probe.

6. The system according to claim 4, wherein the predetermined position is located half-way between the first terminal and the second terminal.

7. The system according to claim 1, wherein the at least one probe conductor and the probe shield are electrically isolated from each other at the second terminal.

8. The system according to claim 7, wherein said predetermined position is located in between the middle of the measurement probe and the second terminal.

9. The system according to claim 1, further comprising at least one reference probe having the same dimensions as the at least one measurement probe, said at least one reference probe being mounted to the conduit and comprising first and second short-circuited terminals where a probe conductor and a probe shield of the reference probe are electrically connected to each other, and said at least one reference probe being exposed to the same temperature environment as the at least one measurement probe, thereby enabling said impedance signals to be compensated for temperature-induced length variations of the at least one measurement probe.

10. The system according to claim 9, wherein said at least one reference probe has the same signal line placement as the at least one measurement probe.

11. The system according to claim 9, comprising:
    a first measurement probe having a first length and a second measurement probe having a second length but otherwise the same dimensions and signal line placement as the first measurement probe, wherein the first length is larger than the second length, thereby enabling signals from the measurement probes to be compensated for erosion induced length variations of the measurement probes;
    a first reference probe having the same dimensions and signal line placement as the first measurement probe, said first reference probe being mounted to the conduit and comprising first and second short-circuited terminals where a probe conductor and a probe shield of the first reference probe are electrically connected to each other, and said first reference probe being exposed to the same temperature environment as the first measurement probe, thereby enabling impedance signals from the first measurement probe to be compensated for temperature induced length variations of the first measurement probe; and a second reference probe having the same dimensions and signal line placement as the second measurement probe, said second reference probe being mounted to the conduit and a comprising first and second short-circuited terminals where a probe conductor and a probe shield of the second reference probe are electrically connected to each other, and said second reference probe being exposed to the same temperature environment as the second measurement probe, thereby enabling impedance signals from the second measurement probe to be compensated for temperature induced length variations of the second measurement probe.

12. The system according to claim 1, comprising a first measurement probe having a first length and a second measurement probe having a second length but otherwise the same dimensions and signal line placement as the first measurement probe, wherein the first length is larger than the second length, thereby enabling said impedance signals to be compensated for erosion induced length variations of the measurement probes.

13. The system according to claim 1, wherein said at least one measurement probe has a coaxial arrangement wherein the dielectric insulator is arranged outside of said at least one probe conductor and said probe shield is arranged outside of the dielectric insulator.

14. The system according to claim 1, wherein said at least one measurement probe comprises a first measurement probe in which the probe conductor, at the second terminal, is galvanically coupled to the probe shield, and a second measurement probe comprising a resistive element at the second terminal which provides a pre-determined impedance between the probe conductor and the probe shield.

15. The system according to claim 1, wherein said at least one measurement probe comprises a first measurement probe which is galvanically connected to the signal processor and a second measurement probe which is capacitively connected to the signal processor.

16. A method for determining at least one parameter of a multiphase fluid comprising hydrocarbons flowing in a conduit of a hydrocarbon processing facility using at least one measurement probe comprising at least one probe conductor, a dielectric insulator arranged outside of the at least one probe conductor, a probe shield arranged outside of the dielectric insulator, a first, open-ended terminal, and a second terminal, the method comprising:
  mounting the at least one measurement probe at the conduit such that the probe conductor, the dielectric insulator and the probe shield, at the first terminal, are coplanar and exposed to the flowing fluid;
  using the at least one measurement probe, measuring impedance signals indicative of at least one physical property of the fluid, which physical property influences the impedance of the first terminal of the at least one probe conductor;
  using a signal line connected to the at least one probe at a predetermined position between the first terminal and the second terminal, conveying the signals from the at least one measurement probe to a signal processor; and
  using the signal processor, processing the signals to determine the at least one parameter, wherein said at least one parameter comprises any one of a flow rate of the fluid, a volume fraction of the fluid, a thickness of a liquid layer or film covering an inside wall of the conduit, and a composition of the liquid layer and/or film.

17. The method according to claim 16, wherein the step of measuring the signals indicative of the least one physical property of the fluid comprises measuring a reflection signal in said at least one measurement probe.

18. The method according to claim 16, wherein the step of using the signal processor to process the signals comprises utilizing a regularization method or an inverse algorithm method to determine the at least one parameter.

* * * * *